US007893024B2

(12) United States Patent
Theil

(10) Patent No.: US 7,893,024 B2
(45) Date of Patent: Feb. 22, 2011

(54) ENHANCEMENT OF IRON CHELATION THERAPY

(75) Inventor: Elizabeth Theil, San Francisco, CA (US)

(73) Assignee: Children's Hospital & Research Center at Oakland, Oakland, CA (US)

(*) Notice: Subject to any disclaimer, the term of this patent is extended or adjusted under 35 U.S.C. 154(b) by 1000 days.

(21) Appl. No.: 11/565,456

(22) Filed: Nov. 30, 2006

(65) Prior Publication Data

US 2009/0215701 A1    Aug. 27, 2009

Related U.S. Application Data

(62) Division of application No. 10/389,424, filed on Mar. 13, 2003, now Pat. No. 7,160,855.

(60) Provisional application No. 60/365,094, filed on Mar. 14, 2002.

(51) Int. Cl.
    *A61K 38/00* (2006.01)
    *C07K 14/00* (2006.01)
(52) U.S. Cl. .......................... 514/6; 530/300; 530/400
(58) Field of Classification Search .................. None
    See application file for complete search history.

(56) References Cited

U.S. PATENT DOCUMENTS

| | | | |
|---|---|---|---|
| 4,528,196 | A | 7/1985 | Pitt |
| 5,013,718 | A | 5/1991 | Adamson et al. |
| 5,430,058 | A | 7/1995 | Shanzer et al. |
| 5,837,677 | A | 11/1998 | Horwitz |
| 5,922,761 | A | 7/1999 | Lai |
| 6,133,322 | A | 10/2000 | Rustin et al. |
| 6,391,852 | B1 | 5/2002 | Feder et al. |
| 6,509,380 | B1 | 1/2003 | Walker, Jr. |
| 2001/0033860 | A1 | 10/2001 | Gwathmey |
| 2001/0039295 | A1 | 11/2001 | Bergeron, Jr. |
| 2003/0104491 | A1 | 6/2003 | Cabantchik |
| 2009/0325869 | A1 | 12/2009 | Theil |

OTHER PUBLICATIONS

Ashley-Koch, A., et al., "Sickle Hemoglobin (Hb S) Allele and Sickle Cell Disease: A HuGE Review," American Journal of Epidemiology, May 1, 2000, pp. 839-845, vol. 151, No. 9.
Calleja, E. M., et al., "Survival and Morbidity in Transfusion-dependent Thalassemic Patients on Subcutaneous Desferrioxamine Chelation," Annals of the New York Academy of Sciences, 1998, pp. 469-470, vol. 850.
Chrichton, R., "Intracellular Iron Storage and Biomineralization," Inorganic Biochemistry of Iron Metabolism: From Molecular Mechanisms to Clinical Consequences, 2001, pp. 133-165, Chapter 6.
Cragg, L., et al., "The Iron Chelator L1 Potentiates Oxidative DNA Damage in Iron-Loaded Liver Cells," Blood, 1998, pp. 632-638, vol. 92, No. 2.

Ha, Y., et al., "Crystal structure of bullfrog M ferritin at 2.8 Å resolution: analysis of subunit interactions and the binuclear metal center," Journal of Biological Inorganic Chemistry, 1999, pp. 243-256, vol. 4.
Hadley, K., et al., "Effects of Dietary Iron on Ferritin Expression and Tissue Iron in Mouse Models for β-thalassemia, and Sickle Cell Trait," Itinerary for The American Society of Hematology 44th Annual Meeting, 1 page, [online] Retrieved from the Internet: <URL: http://www.abstracts-on-line.com/abstracts/hemphiladelphia02/aol.asp>.
Hagar, W., et al., "A Molecular Basis for Resistance to Liver Damage from Transfusional Iron Overload in Sickle Cell Disease," Itinerary for The American Society of Hematology 44th Annual Meeting, Dec. 9, 2002, 1 page, [online] Retrieved from the Internet: <URL: <http://www.abstracts-on-line.com/abstracts/hemphiladelphia02/aol.asp>.
Harmatz, P., et al., "Organ Injury in Chronically Transfused Patients with β Thalassemia or Sickle Cell Disease," Itinerary for The American Society of Hematology 44th Annual Meeting, Dec. 7, 2002, 1 page, [online] Retrieved from the Internet: URL: <http://www.abstracts-on-line.com/abstracts/hemphiladelphia02/aol.asp>.
Jones, K., et al., "Formation of a linear [3Fe-4S] cluster in a seven-iron ferredoxin triggered by polypeptide unfolding," Journal of Biological Inorganic Chemistry, 2002, pp. 357-362, vol. 7.
Kontoghiorghes, G. J., et al., "Iron chelation studies using desferrioxamine and the potential oral chelator, 1,2-dimethyl-3-hydroxypyrid-4-one, in normal and iron loaded rats," Journal of Clinical Pathology, 1987, pp. 404-408, vol. 40.
Murray-Kol, L. E., et al., "Women with low iron stores absorb iron from soybeans," American Journal of Clinical Nutrition, 2003, pp. 180-184, vol. 77.
Olivieri, N. F., et al., "Iron chelating therapy and treatment of thalassemia," Blood, 1997, pp. 739-761, vol. 89, No. 3.
Olivieri, N. F., et al., "Long-Term Safety and Effectiveness of Iron-Chelation Therapy with Deferiprone for Thalassemia Major," N. Engl. J. Med., 1998, pp. 417-423, vol. 339, No. 7.
Richardson D. R., et al., "Development of Iron Chelators to Treat Iron Overload Disease and Their Use as Experimental Tools to Probe Intracellular Iron Metabolism," Am. J. Hematol., 1998, pp. 299-305, vol. 58.
Takagi, H., et al., "Localized Unfolding at the Junction of Three Ferritin Subunits," The Journal of Biological Chemistry, May 8, 1998, pp. 18685-18688, vol. 273, No. 30.
Theil, E. C. et al., "Ferritin," Handbook of Metalloproteins, 2001, pp. 771-781.

(Continued)

*Primary Examiner*—Anand U Desai
(74) *Attorney, Agent, or Firm*—Fenwick & West LLP

(57) ABSTRACT

The present invention provides methods of enhancing the rate of iron release from ferritin. By increasing the amount of iron available for chelation, the invention also provides methods of treating conditions associated with iron overload. The invention also provides in one embodiment agents which are useful for treating iron overload.

14 Claims, 12 Drawing Sheets

OTHER PUBLICATIONS

Trikha, J., et al., "High Resolution Crystal Structures of Amphibian Red-Cell L Ferritin: Potential Roles for Structural Plasticity and Salvation in Function," Journal of Molecular Biology, 1995, pp. 949-967, vol. 248.

Xiaofeng L., et al., "Opening protein pores with chaotropes enhances Fe reduction and chelation of Fe from the ferritin biomineral," Proceedings of the National Academy of Sciences, Apr. 1, 2003, pp. 3653-3658.

Weili, J., et al., "'Opening' the Ferritin Pore for Iron Release by Mutation of Conserved Amino Acids at Interhelix and Loop Sites," Biochemistry, 2001, pp. 7525-7532, vol. 40, No. 25.

PCT International Search Report, PCT/US03/08212, Sep. 2, 2003, 5 pages.

Liu, X., et al., "Peptides Selected for the Protein Nanocage Pores Change the Rate of Iron Recovery from the Ferritin Mineral," The Journal of Biological Chemistry, Nov. 2, 2007, pp. 31821-31825, vol. 282, No. 44.

SEQUENCE LISTING

<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic -continued example peptide

<400> SEQUENCE: 1

Ser Gln Val Arg Gln Asn Tyr His
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      example peptide

<400> SEQUENCE: 2

Ser Gln Ile Arg Gln Asn Tyr Ser
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      example peptide

<400> SEQUENCE: 3

Arg Gln Val Arg Gln Asn Phe His
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      example peptide

<400> SEQUENCE: 4

Gln Arg Val Arg Gln Asn Phe His
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      example peptide

<400> SEQUENCE: 5

Ser Gln Val Asp Gln Asn Tyr His
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      example peptide

<400> SEQUENCE: 6

Ser Gln Val Asp Gln Asn Phe His
 1               5

<210> SEQ ID NO 7

```
<211> LENGTH: 8
<212> TYPE: PRT
<213> ORGANISM: Artificial Sequence
<220> FEATURE:
<223> OTHER INFORMATION: Description of Artificial Sequence: Synthetic
      example peptide

<400> SEQUENCE: 7

Ser Gln Ile Asp Gln Asn Tyr Ser
 1               5
```

ENHANCEMENT OF IRON CHELATION THERAPY

CROSS REFERENCE TO RELATED APPLICATIONS

This application is a division of U.S. application Ser. No. 10/389,424, filed Mar. 13, 2003, now U.S. Pat. No. 7,160,855, which claims the benefit of U.S. Provisional Application No. 60/365,094, filed Mar. 14, 2002, which are both hereby incorporated in their entirety by reference.

STATEMENT REGARDING FEDERALLY SPONSORED RESEARCH OR DEVELOPMENT

The U.S. Government has certain rights in this invention pursuant to Grant No. DK20251 awarded by the National Institutes of Health.

BACKGROUND OF THE INVENTION

1. Field of the Invention

The invention relates to methods and compositions useful for enhancing iron release from ferritin, including methods and compositions useful for treatment of iron overload.

2. Description of the Related Art

The Biochemistry of Iron Storage

Iron biochemistry is complex and highly regulated. Several carriers are involved in iron transport, including the protein transferrin. The majority of stored iron in bodily tissues is in the protein ferritin, which has the same function in animals, plants and bacteria. In healthy individuals, approximately 1-12% of total body iron is stored in ferritin. In patients with iron overload, this value is much greater.

Ferritin is a 24 subunit protein that forms a large cavity (8 nm) that concentrates up to 4,500 iron atoms as a solid mineral, although the "nano-rock" is normally found with closer to 30% of this value. In animals, ferritin is present both in serum and in tissues, especially in the liver and in bone marrow where it serves as an iron reserve for the production of hemoglobin; the serum form of ferritin, which contributes little to overall iron storage, nevertheless finds clinical use as a reporter of body iron levels. Ferritins occur in animals as approximately 25 distinct isoforms depending on their proportions of the two primary subtypes of ferritins, H or L. These distinct subtypes also differ in their rates and mechanisms of iron oxidation, core formation and iron turnover. The active sites in H-type ferritin rapidly increase, by a factor of $10^4$, the rate at which the mineral core is created, at the expense of producing some hydrogen peroxide. L-type ferritin subunits lack the residues necessary to form an active site. See, e.g., Theil, E. C. in *Handbook of Metalloproteins*, (A. Messerschmidt et al., eds.), John Wiley & Sons, Chichetser, pp. 771-781 (2001); Andrews, S. C. *Adv. Microb. Physiol.* 40:281-351 (1998); Chasteen, N., Harrison, P., *J. Struct. Biol.* 126:182-194 (1999); Harrison, P., Arosio, P., *Biochem. et Biophys. Acta* 1275:161-203 (1996).

Iron uptake by ferritin results in the formation of an oxidized Fe(III) mineral. Iron release from ferritin can be effected through treatment with various reductants in vitro and in vivo. The size of the reductant has no effect on the rate of reductive release of iron (Watt G. D., et al., *Proc. Natl. Acad. Sci. USA.* 82:3640-2643 (1985); Watt G. D., et al., *Proc. Natl. Acad. Sci. USA* 85:7457-7461 (1988)).

Structural studies on ferritin and ferritin mutants have helped to clarify the mechanism of iron release. Structure at the junction of three subunits in ferritin creates "pores" through which iron exits from the hydrated ferric oxide core. There are eight three-fold junctions in each ferritin molecule. Structural studies of a mutant form of ferritin (H-L 134P) showed a region that became disordered in the crystal structure as a result of a mutation that locally disrupted the structure of the protein at the three-fold junctions (Takagi H., et al. (1998) *J. Biol. Chem.* 273:18685). Measurements of iron release rates showed that the iron can be cleared from the mutant proteins, in test environments, within five minutes compared to 150 minutes in the closed ferritin protein.

Another structural study focused on a larger set of mutants that were expected to affect the geometry or charge of conserved amino acids at the three-fold junctions (Jin, W. et al., *Biochemistry,* 40: 7535-7532 (2001)). Alterations of a conserved hydrophobic pair, a conserved iron pair, and a loop at the ferritin pores to which no other function had been assigned, all increased iron exit by 3-30 fold, with no apparent effect on ferritin assembly except for a slight decrease in volume. The pores in these mutants appear to be "locked" in the "open" position.

Iron Overload

Iron overload is a complication of the treatment, by chronic transfusion, of a number of genetic diseases associated with inadequate red cell production (anemias) and of other genetic diseases that lead to excessive iron absorption from the diet. Two relatively common anemic conditions that can result in iron overload from hypertransfusion are sickle cell disease and thalassemia. Iron overload is a serious condition that can cause fatal cardiac damage or stroke if left untreated. See, e.g., Golden, C. et al., *Curr. Opin. Hematol.,* 5(2):89-92 (1998). Since the genes responsible for the diseases that lead to iron overload (either congenitally or indirectly from transfusion treatment) are very common in the population, the combined frequency of carriers for the diseases that can involve iron overload approaches 20% in North American and European populations. In Africa, Southeast Asia, and the Mediterranean, where malaria is endemic, and among the descendents of such populations world-wide, single gene mutation frequencies are as high as 10%. See Ashley-Koch, A. et al., *Amer. J. Epid.,* 51(9): 839-45. Worldwide, hundreds of thousands of people suffer from iron overload and a billion suffer from other abnormalities of iron homeostasis.

Current Treatments

Currently, iron overload from excess absorption is treated by regular phlebotomy (bleeding), while iron overload from hypertransfusion is treated by long periods of intravenous or subcutaneous administration (up to 8 hours/day for at least 5 days/week) of an iron chelator. Clinically used chelators are designed to bind extracellular iron and to pull the iron from intracellular sites. Such an indirect approach leads to the necessity of the long exposure periods.

In spite of the many efforts to develop new and enhanced chelation treatments for iron overload, the best treatment available remains intravenous or subcutaneous administration of desferrioxamine (e.g., Desferal®). Although desferrioxamine treatment is effective and safe, a number of side effects have been observed, including inhibition of growth, bone abnormalities, retinal damage, ocular toxicity and ototoxicity (Hoffbrand, A. V., *Curr. Op. Hematol.* 2:153-158 (1995)). In addition, desferrioxamine administration may also lead to an allergic response through the activation of mast cells (Magro, A. M., Brai M., *Immunology* 49:1 (1983); Shalit, M., et al., *J. Allergy Clin. Immunol.* 88:854 (1991); Lombardo, T., et al., *Am. J. Hematol.* 51:90 (1996)). This allergic response can lead to pain and irritation at the point of injection.

More limiting to the current therapeutic approaches is the issue of patient compliance. The necessity of slow infusion of the chelator over a period of 8-24 hours a day makes patient compliance a serious issue in the treatment. The occurrence of side effects, especially allergic reaction, irritation or pain, encourages lack of compliance. Another problem with the current method of treatment is that such long-term treatment is also expensive and impractical for most of the world's population. The drug itself, desferrioxamine, is also expensive.

Richardson and Ponka have proposed requirements for the development of improved iron chelators for the treatment of iron overload (Richardson D. R., Ponka P., *Am. J. Hematol.* 58:299-305 (1998)). Briefly, the chelator should be: (1) biospecific, having high affinity for iron over other physiologically important cations, and for stored iron rather than iron functioning in important enzymes such as hemoglobin; (2) bioavailable, and preferably orally available; (3) stable to degradation by enzymes; (4) biocompatible, with minimal side effects; (5) highly effective at promoting iron excretion; and (6) readily and inexpensively synthesized.

Following these criteria, major efforts have been undertaken to develop new iron chelators that are orally available for the treatment of iron overload. Desferrioxamine, for instance, can be administered orally but oral administration greatly reduces its efficacy as compared to either intravenous or subcutaneous administration (Katramis C., et al., *Lancet* 1:51 (1981)). Newer chelating agents are also under consideration, but of the siderophore class of chelators, desferrioxamine has proved to be the most effective for treating iron overload (Richardson D. R., Ponka P., *Am. J. Hematol.* 58:299-305 (1998)). Also under consideration is the α-ketohydroxypyridone chelator 1,2-dimethyl-3-hydroxypyrid-4-one, variously known as deferiprone, L1 or CP20. However, recent clinical data have shown that deferiprone is not completely effective at managing iron overload and may worsen hepatic fibrosis (Olivieri, N. F. & Brittenham, G. M., *Blood* 89:739 (1997); Olivieri, N. F., et al., *N. Engl. J. Med.* 339: 417-423 (1998)).

While the references mentioned above for suggested improvements to chelators are relevant to understanding the problem of iron overload, they do not teach a solution to the problem of treatment of iron overload. Among other disadvantages, none of the references teaches how to enhance the rate of iron release from native ferritin, such that chelation of released iron is facilitated. Thus, there is a clear need for more efficacious methods of treating iron overload, in addition to methods and reagents useful for the identification and characterization of compounds which enhance iron release from ferritin. The present invention addresses these and other shortcomings of the prior art.

SUMMARY OF THE INVENTION

In one aspect, the present invention provides a method for enhancing iron release from ferritin. The method involves the use of a protein unfolding agent in conjunction with an iron chelator. In a preferred embodiment, ferritin is exposed to a protein unfolding agent at concentrations of the agent effective to enhance the rate of iron release from ferritin upon addition of a chelating agent and a reducing agent. A reducing agent is necessary when practicing the method in vitro, but not in vivo. In a preferred embodiment, the unfolding agent locally alters the structure of ferritin at the junction of three subunits, e.g., at the ferritin pore, or at the site of iron release, e.g., the C, D loop and helices, but does not promote ferritin disassembly, generalized unfolding, or global denaturation.

In a preferred embodiment, the protein unfolding agent is added simultaneously with an iron chelator. In another embodiment, the protein unfolding agent and the iron chelating agent are the same compound, e.g., they are coupled.

In one aspect of the invention, the protein unfolding agent is Triton X-100, but other non-ionic detergents can also be used. Using the methods of the present invention, Triton X-100 in combination with the chelator 2,2' bipyridine produces a significant (2-3 fold) increase in the initial rate of iron release and a 10 to 20-fold decrease in the time to release 50% of the total iron in ferritin. The most effective concentration of Triton-X-100 is approximately 1.0-10% (volume/volume).

Protein unfolding agents include non-detergent chaotropic agents that disrupt the structure of ferritin pores without denaturing or causing disassembly of ferritin. These are also useful for practicing the invention. In particular, agents that destabilize the region of the structure previously identified as a site of iron release, namely the CD loop and helices (Takagi H., et al., *J. Biol. Chem.* 273:18685-18688 (1998)), are effective at increasing the rate of iron release from ferritin.

One such chaotropic agent is urea, but other chaotropic agents can be used, e.g., guanidine HCl. Using the methods of the present invention in vitro, urea, in combination with the chelator 2,2'-bipyridine and reductant, causes a 2-4 fold increase in the initial rates of iron release and a 10-fold decrease in the time required to remove 50% of the total iron in ferritin. Surprisingly, concentrations of chaotropes such as urea that are much lower (e.g., 0.001-1 M) than the concentrations commonly used to denature proteins (6-10 M) are most effective. At concentrations of urea higher than the effective concentrations, the rate of iron release from ferritin is not significantly enhanced.

In one embodiment of the invention, the above methods and reagents are used to treat transfusional iron overload, or diseases associated with iron overload, in a living organism. In a preferred embodiment, the organism is an animal, preferably a primate, and most preferably, a human. In general, because the environment in vivo is sufficiently reducing, non-endogenous reductants will not be necessary to practice the methods of the invention in vivo.

The invention also encompasses compositions for treatment of iron overload. The compositions of the invention include an effective amount of a protein unfolding agent and a pharmaceutical excipient. The composition can be suitable for IV administration. In one embodiment, the composition includes an iron chelator.

In another aspect, the invention encompasses methods to identify agents that alter the rate of release of iron from ferritin. In this embodiment, a solution of reconstituted ferritin is prepared having a substantially uniform iron content. One portion of this solution is treated with an agent of interest, while the other is left untreated. A chelating agent and a reductant are added to both solutions to initiate iron release. If necessary, a reagent to facilitate the detection of released iron can also be added. The rates of iron release from ferritin in the two solutions are measured and compared to identify whether the agent enhances the rate of iron release from ferritin. This method can be extended to find biological components that directly regulate ferritin release in vivo.

In one variation of the method for identifying useful agents, the iron content of ferritin is between 50 and 4000 atoms. Preferably the iron content is approximately 500 atoms.

Another embodiment of the invention includes a kit comprising reagents useful for identification of agents that alter rates of iron release from ferritin and, optionally, instructions for use.

The methods and compositions of the invention can include numerous chelators. Preferred chelators include 2,2' bipyridine, desferrioxamine or derivatives thereof. The chelator can include a calorimetric indicator of iron binding. A preferred chelator of the invention for in vivo applications is desferrioxamine. Chelators can exist separately from the unfolding agents of the invention, or they can be chemically linked to the unfolding agents. A single molecule that has both chelating and protein unfolding properties suitable for carrying out the methods of the invention can be used.

BRIEF DESCRIPTION OF THE SEVERAL VIEWS OF THE DRAWING

These and other features, aspects, and advantages of the present invention will become better understood with regard to the following description, and accompanying drawings, where:

FIG. 1 shows the enhancement of iron release after treating ferritin with low concentrations of protein unfolding agents by monitoring formation of Fe(II)-bipyridyl at absorbance at 522 nm.

FIG. 2 illustrates enhancement of iron release after treating ferritin with low concentrations of protein unfolding agents.

FIG. 3 illustrates sub-domain helix reversible unfolding in the ferritin four helix bundles.

DETAILED DESCRIPTION OF THE INVENTION

Definitions

Figure 1A:
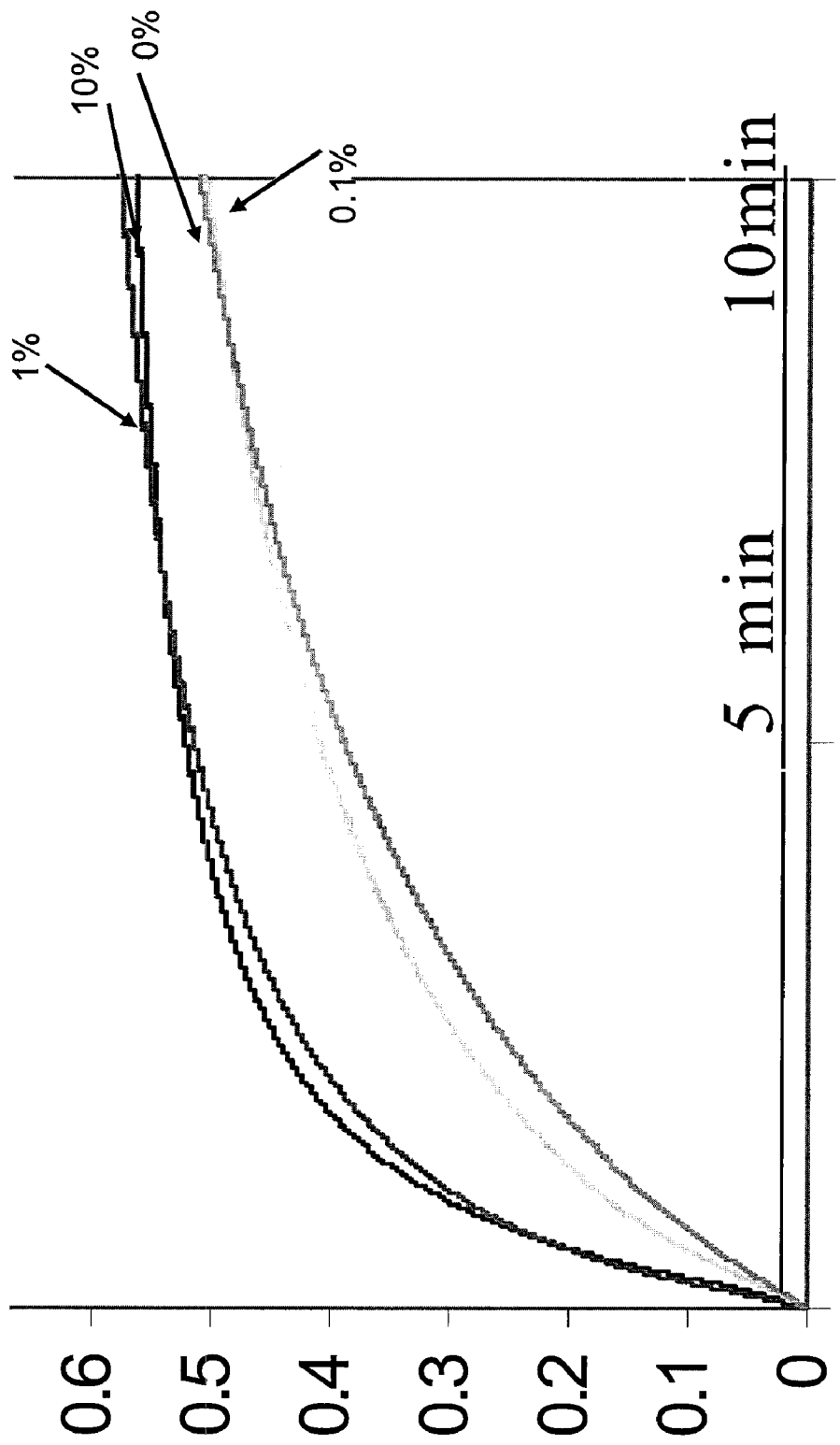
FIG. 1A is a progress curve for formation of Fe(II)-bipyridyl by ferritin after treatment with Triton-X-100 (0%, 0.1%, 1% and 10%, volume/volume).

As used in this specification, the term "ferritin" means a protein that has biological and/or chemical activity and structure the same as, or substantially similar to, a natural ferritin. As such, ferritin includes a naturally occurring ferritin protein or a recombinant, reconstituted ferritin protein, comprising 12 or 24 ferritin subunits, wherein the subunits associate to form a spherical particle. Natural ferritins include human ferritin, ferritin from other animals (ferritin derived from horse spleen or bullfrogs, for example), plant ferritin (derived from soybeans, for example), mycoferritin (derived from fungi), or bacterial ferritin. Ferritin includes recombinant ferritin expressed by genetically-transformed microorganisms such as *E. coli*, and other bacteria and yeasts. Ferritin expressed by genetically-transformed or recombinant microorganisms can have an amino acid sequence identical or analogous to a natural ferritin. The term ferritin can include one or both isoforms, H and L.

A "ferritin subunit" is defined as one of the 12 or 24 subunits that make up a ferritin protein. The numbering system used herein for the identification of amino acids within ferritin subunits is based on the original sequence of horse spleen L ferritin (Swiss Protein Database Accession Number P02791). The horse spleen numbering system can be easily converted to a numbering system based on the human H sequence (Swiss Protein Database accession number P02794; the human L sequence accession number is P02792), which has four additional amino acids at the N-terminus. The human H sequence numbering therefore adds 4 to the corresponding amino acid number in horse spleen ferritin. For example, L134 by horse spleen numbering corresponds to L138 by human H sequence numbering. Alignments of ferritin subunit sequences can be found, e.g., in Theil, E. C., in: *Handbook of Metalloproteins*, (Messerschmidt, A. et al., eds.), John Wiley & Sons, Chichester, UK, pp. 771-81 (2001); Harrison, P. M. & Arosio, P. (1998); Andrews, S. C., et al., *J. Inorg. Biochem.* 47: 161-174; Waldo, G. S. & Theil, E. C., (1996) "Ferritin and Iron Biomineralization" in: *Comprehensive Supramolecular Chemistry*, Vol. 5, (K. S. Suslick, ed.), Pergamon Press, Oxford, UK, pp. 65-89.

"Apoferritin" is ferritin in the unmineralized state.

A "ferritin pore" is one of eight pores in an assembled ferritin protein formed by trimers of ferritin subunits. In an intact ferritin protein, there are eight three-fold axes of symmetry, each at a junction of three ferritin subunits. Each ferritin pore is formed by these three-way junctions of ferritin subunits. The pores can be visualized in crystals of ferritin proteins by X-ray crystallography.

A "protein unfolding agent" is any compound capable of destabilizing the secondary, tertiary, or quaternary structure of a protein. Destabilization of protein structure can be effected by interference with ionic, hydrophobic, or Van der Waals interactions between amino acid residues of the protein, or by interference with interactions between the protein and solvent (usually water). Examples of protein unfolding agents are well known to those of skill in the art and include but are not limited to urea, guanidine-HCL, Triton X-100, and the like.

The term "near" or "adjacent to" when used to indicate a location with respect to a particular amino acid residue (a "reference residue") refers to a residue covalently attached to the reference residue, either preceding or following that residue, or in Van der Waals contact with the reference residue.

The term "treatment" as used herein covers any treatment of a condition treatable by an iron chelator in a living organism, preferably a primate, and more preferably a human, and includes:

(i) preventing the condition from occurring in a subject which can be predisposed to the condition but has not yet been diagnosed as having it;

(ii) inhibiting the condition, e.g., arresting or slowing its development; or (iii) relieving the condition, e.g., causing regression of the condition.

Stated quantities in the specification and claims are intended to encompass variations of the stated amounts consistent with the practice of the present invention. Such variations are readily determined by one of skill in the art following procedures outlined in specification and typically encode variation on the order of +/−10-20%.

Enhancement of Iron Release from Ferritin

In one embodiment, the invention provides for a method of enhancing the release of iron from ferritin by exposing ferritin to a protein unfolding agent. The protein unfolding agent is present in solution at concentrations that are effective to enhance iron release from ferritin without causing disassembly of ferritin into ferritin subunits, or causing generalized unfolding of the protein, e.g., global denaturation. In some embodiments of the invention, the rate of iron release is not significantly enhanced at concentrations higher than the effective concentrations compared to the rate of iron release in the absence of the protein unfolding agent.

Without wishing to be bound by theory, it is believed that the method enhances iron release, in part, by the destabilization of protein structure at or near the ferritin pores, which are differentially sensitive to the unfolding agents. In particular, it is believed that effective concentrations of some protein unfolding agents cause localized disordering of helix packing between residues 110 and 135 of the ferritin subunits. The disordering is believed to result in an "opening" of the ferritin pores, allowing easier access of iron to chelators and/or reductants.

A preferred protein unfolding agent is one that enhances iron release by selectively unfolding ferritin pores, without causing ferritin disassembly. One skilled in the art will recognize that a protein unfolding agent can include a wide variety of chemicals, including, but not limited to, small molecules, e.g., non-ionic detergents or non-detergent chaotropes, peptides, antibodies, chaperoning, nucleic acids, and other bioactive agents.

In one embodiment of the invention, the protein unfolding agent is capable of disassembling or denaturing ferritin at high concentrations, but is used at a lower concentration to enhance iron release without denaturing ferritin. In a preferred embodiment, the concentration for effecting enhanced iron release is less than one-tenth the concentration of a given protein unfolding agent that would lead to ferritin disassembly under otherwise identical conditions. Disassembly can be detected by standard biochemical assays such as non-denaturing gel electrophoresis, velocity sedimentation, isopycnic centrifugation, size-exclusion chromatography, or spectrophotometry.

Protein unfolding agents suitable for practicing the invention include, but are not limited to, non-ionic detergents such as Triton X-100, Triton X-114, Tween 20, Tween 40, Tween 60, Tween 80, Brij-35 and the like. Such detergents are typically referred to as "non-denaturing" detergents. In a preferred embodiment, enhanced iron release by ferritin is effected by the addition of Triton X-100 to final concentrations of approximately 1.0-10% (volume/volume).

In another embodiment of the invention, the protein unfolding agent is a non-detergent chaotropic agent such as urea. Urea is well-known to those skilled in the art as a protein denaturant at concentrations above 6 M, although global ferritin structure is impervious to these concentrations under physiological conditions. In a preferred embodiment, the urea is present in concentrations of 1-10 mM. Other non-detergent agents with chaotropic properties similar to urea, e.g., guanidine hydrochloride, can also be used to practice the methods of the invention. Analogues of urea or guanidine hydrochloride, such as hydroxyurea, can also be useful for practicing the methods of the invention.

In yet another embodiment of the invention, the protein unfolding agent is a peptide. Peptides are selected that bind specifically to the ferritin pore, and enhance iron release of wild type H-ferritin ("closed" pore) but do not bind to an "open"/disordered pore (e.g., ferritin mutant H-L134P) to distinguish peptides recognizing generic ferritin features from those recognizing closed ferritin pores. The peptide is coupled to a chelator using, e.g., t-Boc. Example peptides that can be used as protein unfolding agents include but are not limited to SQVRQNYH (SEQ ID NO:1), SQIRQNYS (SEQ ID NO:2), RQVRQNFH (SEQ ID NO:3), QRVRQNFH (SEQ ID NO:4), SQVDQNYH (SEQ ID NO:5), SQVDQNFH (SEQ ID NO:6), and SQIDQNYS (SEQ ID NO:7).

In a preferred embodiment, an iron chelator is present in solution with the ferritin, reductant, and the protein unfolding agent. The iron chelator binds the iron that has been reduced and released or loosened from the ferritin mineral after ferritin has been treated with a protein unfolding agent, or the chelator can interact with iron, which remains associated with the protein or mineral. Any iron chelator can be used in the method, including bidentate chelators, or, preferably, hexadentate chelators. Bidentate chelators, such as ferrichrome, coordinate with only two of the six coordination sites in free iron. Hexadentate chelators coordinate with all six coordination sites of iron. An example of a preferred hexadentate chelator is desferrioxamine (e.g., Desferal®, DFO, deferoxamine, deferoxamine mesylate, deferoxamine methanesulfonate, desferrioxamine mesylate). Hexadentate chelators are preferred because they interact with iron in a one to one ratio, reducing the amount of chelator needed to bind a given amount of iron. Chelators that preferentially bind either Fe(III) or Fe(II) can be used.

Other iron chelators useful within the scope of the present invention include, for example, Deferipone, PIH (pyridoxal isonicotinoyl hydrazone and analogues), Rhodotorulic acid, HBED (N,N'-Bis(2-hydroxybenzyl)ethylenediamine-N,N-diacetic acid), HBPD (N,N'-Bis(2-hydroxybenzyl)propylene-1,3-diamine-N,N-diacetic acid), 2,3-dihydroxybenzoic acid, DTPA (diethyltriamine pentaacetic acid) and iron chelators produced by bacterial siderophores.

In one variation of the method, an iron chelator is covalently attached, e.g., coupled, to the protein unfolding agent. In this embodiment, a single agent includes a protein unfolding activity and a chelating activity. The protein unfolding and chelating moieties of this embodiment can be coupled using any one of many possible chemical methods and compositions. Preferably, the solubility or cell permeability of a protein unfolding agent will not be substantially decreased by its conjugation with an iron chelating moiety. Similarly, a conjugated agent will preferably be no more toxic and, more preferably, substantially less toxic, than its unconjugated components.

Treatment of Iron Overload

One aspect of the present invention provides a method of treating a primate, particularly a human, which has a condition that is treatable by an iron chelator. The method includes the administration of therapeutically-effective amounts of an iron chelator and a protein unfolding agent. In a preferred embodiment, the administration is oral, parenteral, or a combination of oral and parenteral administration routes. A condition treatable by an iron chelator can occur, e.g., through a genetically determined error that results in increased absorption of iron from a normal diet or can occur through repeated blood transfusions to treat a disease state. Such conditions in which iron chelators can be used include malaria, cancer, HIV infections, inflammatory bowel disease, host v. graft rejection, graft v. host rejection, reperfusion injury, neurological disorders, and iron overload. The condition in which this method is most useful is "iron overload." This condition is characterized by greater than normal focal or generalized deposition of iron within body tissues.

When such focal or generalized deposition is associated with tissue injury, with total body iron greater than about 15 grams, it is known as hemochromatosis, which can be primary or secondary. Primary hemochromatosis most commonly arises from an autosomal recessive trait linked to the histocompatibility locus on human chromosome 6 that results in increased absorption of iron from a normal diet. This form of primary hemochromatosis affects 3 to 8 people per thousand. Primary hemochromatosis can also occur as a result of other genetically determined errors including conditions identified as atransferrinemia, thalassemia major, and y-linked hypochromic anemia. While the Merck Manual, 15th Edition, sets forth the classification of these conditions, differential diagnosis is difficult. Diagnosis will depend on the history of iron administration, the examination of relatives of the patient, the degree of iron overload, and the presence or absence of localizing signs.

Hemochromatosis rarely occurs before middle age. Typical manifestations are cirrhosis of the liver, brown pigmentation of the skin, diabetes mellitus, and cardiomyopathy, which can be manifested by cardiomegaly, congestive failure, and arrhythmias or conduction disturbances. In the case of pituitary failure, testicle atrophy and loss of libido can be seen. Abdominal pain, arthritis and chondrocalcinosis occur less often.

Focal hemosiderosis (the accumulation of hemosiderin in tissues) chiefly occurs in the lungs and kidneys. Pulmonary hemosiderosis may be due to recurrent pulmonary hemorrhage that occurs as an idiopathic entity, e.g., as part of Goodpasture's Syndrome.

Diagnosis of the above-mentioned conditions can be found in Merck's Manual. Each of these conditions should be considered as a condition that is treatable by an iron chelator.

Secondary hemochromatosis or hemosiderosis can result from increased parenteral iron intake such as through repeated transfusion (transfusional siderosis). Repeated transfusions are often required for various diseases, such as, for example, Sickle-Cell Disease, Thalassemia (Cooley's anemia), and myelodysplasia. Secondary hemochromatosis or hemosiderosis can also be caused by iron dextran taken intramuscularly, increased iron absorption due to increased iron ingestion, or may be due to anemia with erythroid hyperplasia, or may possibly be linked to megadoses of Vitamin C. Focal hemosiderosis may be pulmonary, renal, or hepatic.

For use in iron overload treatment, a protein unfolding agent must meet the following criteria. First, the agent must be pharmacologically compatible, with few known side effects, and capable of permeating living cells. The protein unfolding agent is administered with an iron chelator. The relative timings of the administration of the unfolding agent and the chelator will depend on their pharmacokinetic properties. The protein unfolding agent and chelator are administered such that an effective dose of each is achieved. The method for determining doses by performing a dose response study is well known in the literature and can be performed for individual patients by monitoring the content of iron that is excreted.

The iron chelator used in the invention is preferably desferrioxamine. Other known chelators that show biological efficacy, such as deferiprone, can also be used. Administration can occur through several means, either orally, intravenously, subcutaneously, or intramuscularly, as discussed in more detail below.

A preferred method of administration of the protein unfolding agent is intravenous administration. "Intravenous administration" means that the drug is delivered in an appropriate composition directly into the veins, e.g., by injection. An intravenous injection can be of a small volume for a short duration, typically via a syringe. Alternatively, an intravenous injection can be of a larger volume for a longer duration, sometimes referred to as an infusion and frequently involving the use of what is known colloquially as an "IV bag" or "IV bottle." The injection or infusion can be of a solution of a formulation comprising the active entity. Generally, the intravenous administration will be done with excipients that are suitable for intravenous administration, which means that the excipients will meet USP considerations in being appropriate for injectable compositions. Thus, the composition will need to be sterile to avoid any complications due to insterility at the injection site.

The amount of the active ingredient that will be present in the composition to be administered is a therapeutically-effective amount, that is, an amount which is sufficient to result in successful treatment as defined above when administered to a subject exhibiting a condition treatable by an iron chelator, e.g., a disease state of iron overload. The therapeutically effective amount will vary depending on the subject and disease state being treated, the severity of the affliction and the manner of administration, and can be determined routinely by one of ordinary skill in the art in light of the disclosure of this specification.

Transfusional iron overload occurs in sickle cell disease and thalassemia. Liver iron concentrations 10-15 above normal, as measured by biopsy, can be observed before chelation therapy and are fatal if left untreated. In sickle cell disease, where the anemia itself may not be fatal, transfusion therapy decreases hospitalizations by more than 10-fold and minimizes stroke. Accepted indications for transfusions include cardiopulmonary symptoms (especially when the hemoglobin count is <5 gm/dL), cardiopulmonary signs (such as high output cardiac failure or hypoxemia) or for other life-threatening conditions which could be alleviated by an increase of oxygen in the blood (such as sepsis, severe infection, cerebrovascular accident, organ failure). Transfusions also reduce surgical morbidity for sickle cell anemia patients. Chronic transfusion therapy appears to limit recurrences of cerebrovascular bleeding and is particularly useful for young patients, under 18 years old, who have had strokes. Chronic transfusion therapy is also indicated where sickle cell disease patients have recalcitrant leg ulcers and may be helpful during pregnancy. Similarly, thalassemia major patients are treated by blood transfusions. Chronic transfusion therapy is valuable in the suppression of abnormal hematopoiesis.

The use of a protein unfolding agent with an iron chelator to prevent iron overload in chronic transfusion therapy is especially important in the treatment of young children with sickle cell disease, as these patients are at increased risk of developing iron overload toxicities and in thalassemia where regular transfusion therapy is continuous.

For a more complete reference to transfusion methods see The Merck Manual, 6th Edition, pp. 1180.

Pharmaceutical Compositions of the Invention

Compositions for treatment of iron overload are also encompassed by the present invention. Said compositions of the invention include an effective amount of a protein unfolding agent and a pharmaceutical excipient. The composition can include an iron chelator. Suitable excipients are well known to one of skill in the art and can be found in, e.g., "Remington: The Science and Practice of Pharmacy" 19th Ed.

In one embodiment, a composition of the invention is the combination of the protein unfolding agent with a pharmaceutical excipient that is suitable for I.V. administration. Generally, the compositions of the invention can fall into one of three (3) categories: 1. a solution that is ready for administration, 2. a dry soluble composition that is ready to be combined with a diluent just prior to use (i.e., reconstitutable), and 3. a liquid concentrate ready for dilution prior to administration.

A reconstitutable composition is a sterile solid packaged in a dry form. A reconstitutable composition is preferred because it is more stable when stored as a dry solid rather than in a solution ready for immediate administration. The dry solid is usually packaged in a sterile container with a butyl rubber closure to ensure the solid is kept at an optimal moisture range. A reconstitutable dry solid is formed by dry fill, spray drying, or freeze drying methods. Descriptions of these methods can be found in Pharmaceutical Dosage Forms Parenteral Medications, Vol. 1, pp. 215-227.

Generally a solution ready for intravenous injection will be a volume greater than 1 ml, preferably more than 10 ml but generally less than 100 ml, although the physician administering the solution must carefully control the rate of administration. Subcutaneous injection is generally limited to a volume of 2 ml, and intramuscular injection is normally limited to 3 ml. Intravenous injection preferably employs dilute aqueous solutions. The I.V. injection should be as close to isotonic as possible to minimize tissue damage and irritation, reduce hemolysis of blood cells, and prevent electrolytic imbalance that can occur during administration. However, it is not always essential that the I.V. injection be isotonic. Intravenous injection allows administration of a solution (along with a blood transfusion, for example) that is not isotonic as long as the administration is slow enough to allow dilution of the solution by the blood. Hypertonic solutions are often used in subcutaneous and intramuscular injections to facilitate absorption of drug due to the resulting local effusion of tissue fluids. However, the injection of hypertonic solutions may cause immediate or delayed pain.

The liquid intravenous compositions are generally dilute and the component present in the highest proportion is the vehicle. The vehicle normally has no therapeutic activity and is nontoxic, but presents the active constituent to the body tissues in a form appropriate for absorption. Absorption normally will occur most rapidly and completely when the protein unfolding agent is presented as an aqueous solution. Limits for particulate matter occurring in intravenous fluids, or large-volume injections used for single-dose infusions, are defined in the USP. Limits also apply to multiple-dose injections, small-volume injections, or injections prepared by reconstitution from sterile solids. The USP defines particulate matter as extraneous, mobile, undissolved substances, other than gas bubbles, unintentionally present in parenteral solutions. The total numbers of particles having effective linear dimensions equal to or larger than 10 µm and larger than 25 µm are counted. The intravenous fluid meets the requirements of the test if it contains not more than 50 particles per mL that are equal to or larger than 10 µm, and not more than 5 particles per mL that are equal to or larger than 25 µm in linear dimension. Preferably, the vehicle of greatest value for this intravenous composition is an aqueous vehicle comprising water that meets the USP specification for water for injection. Generally, water of suitable quality will either be prepared by distillation or reverse osmosis to meet these USP specifications. The appropriate specifications are spelled out in "Remington: The Science and Practice of Pharmacy" 19th Ed. at pp. 1526-1528.

Additional substances can be included in the intravenous compositions of this invention to improve or safeguard the quality of the composition. Thus, an added substance can affect solubility, provide for patient comfort, enhance the chemical stability, or protect the preparation against the growth of microorganisms. Thus, the composition can include an appropriate solubilizer, substances to act as antioxidants and substances that act as a preservative to prevent the growth of microorganisms. These substances will be present in an amount that is appropriate for their function, but will not adversely affect the action of the composition as a treatment for iron overload. Examples of appropriate antimicrobial agents include thimerosal, benzethonium chloride, benzalkonium chloride, phenol, methyl p-hydroxybenzoate and propyl p-hydroxybenzoate. Appropriate antioxidants can be found in Remington at p. 1529.

If needed, the addition of a buffer to the intravenous composition prevents changes in pH of the composition that can occur during storage due to breakdown of components or interaction with the container or the atmosphere. The ideal buffer system should have a buffer capacity adequate to maintain the pH of the preparation at a stable storage value while permitting the preparation to adjust to the pH of the blood as the preparation is introduced into the body. Ideally, the pH of the buffer will be about pH 7.4, the pH of the blood. pH values that vary significantly from pH 7.4 can cause complications. Fluids that have a pH of above 9 can cause tissue necrosis when introduced into the body. Fluids with a pH of below 3 can cause extreme pain and phlebitis after administration. For intravenous preparations, a wider range of pHs is acceptable particularly if the solution is to be added to transfusion fluid. The pH of solutions to be administered by IV should fall within the range of 3.0-10.5. This increase in range is allowed because of the buffering capacity of the blood. A suitable buffer system can be designed for specific drugs from knowledge of the pH profile of the drug in solution. Other methods of administration, such as subcutaneous and intramuscular injections, require that the solution fall within a narrower pH range of 4.0 and 9.0.

Except insofar as any conventional media or agent is incompatible with the active compound, use thereof in the therapeutic compositions is contemplated. Supplementary active compounds can also be incorporated into the compositions, such as liposomes that can facilitate delivery of the compositions to cells.

Determination of the Toxicity of the Protein Unfolding Agent and Chelator

The toxicity of an effective amount of protein unfolding agent in the presence or absence of a chelator can be determined in vitro by techniques well-known to those skilled in the art, e.g., by the trypan blue exclusion assay.

Toxicity in the in vivo administration of an agent for enhancing iron release and a chelator, e.g., desferrioxamine combined with a protein unfolding agent, e.g., urea, can be tested in animal models, e.g., guinea pigs. Similar studies can be applied to Mongolian gerbils, rats with iron-overload, and transgenic mouse models of thalassemia (e.g., mice with at least one ablated globin gene; mice with human HbS genes, etc.).

For example, two species of normal animals and iron-overloaded animals can be compared. One group of animals receives a composition comprising desferrioxamine and the protein unfolding agent, and another group receives a similar composition without desferrioxamine. Animals are monitored for cardiac arrhythmias via electrocardiogram once a week. Heart function is determined with echocardiography at the same time that electrocardiograph recordings are made at one and at 24 hour intervals post-injection followed by weekly monitoring for up to 6 weeks. Full necropsy is performed with special attention to harvesting the liver and heart. Cardiac and liver functions are monitored in the animals after one hour, 24 hours, and at weekly intervals up to ten weeks following administration.

Dosing range, safety, and toxicity studies in normal animals, as well as quantification of any toxicity seen in the liver, heart, gastrointestinal tract, kidney, and at the injection site is important. At the time of full body necropsy tissue weights and gross appearance is recorded. The heart and liver are stored in 10% phosphate buffered formalin. Other body organs are also stored in 10% buffered formalin for future light miscroscopy, or special staining. Prussian blue iron stain is applied to liver and heart samples. Quantitative analysis can be used. A single observer should make all measurements.

Flame photometry atomic absorption spectroscopy measurements are carried out on fresh or lyophilized liver and heart with either normal iron depot or iron-overload with or without administration of the protein unfolding agent. Normal animals treated with Applicant's combination of protein unfolding agent and iron chelator is compared to non-treated animals for possible reduction in normal iron levels.

Determination of the Biological Half-Life of the Protein Unfolding Agent

The biological half life of a protein unfolding agent useful for, e.g., treatment of iron overload, can be determined using assays well known to one of skill in the art. Pharmacokinetic studies can be performed in both iron overloaded and normal animals with compositions comprising a protein unfolding agent and an iron chelator. Pharmacokinetic parameters can be calculated using a curve fitting program such as KINFIT. The half-life of blood levels of the protein unfolding agent can thus be determined.

Identification of Agents that Enhance Iron Release from Ferritin

One aspect of the invention provides a method for identification of agents that alter, e.g., enhance, iron release from ferritin. Agents found by the method of the invention can be useful for the study of ferritin biochemistry. Alternatively, the agents can be particularly useful for the treatment of illnesses associated with iron overload.

For the purposes of this method, the use of recombinant ferritin with a relatively uniform iron distribution is preferred. Methods for reconstitution of recombinant ferritin subunits are well-known in the art, as exemplified by, e.g., Takagi, H. et al., *J. Biol. Chem.* 273:18685-18688 (1998). An iron content in the range of 400 to 600 atoms per molecule is preferred, but other amounts can also be used, provided they permit iron release from reconstituted ferritin to be accurately measured and compared.

According to one embodiment of this method, solutions of the reconstituted ferritin protein in the presence of a chelating agent and a reductant are treated with at least one agent of interest, e.g., potential protein unfolding agents, either known or unknown, and the release of iron from the ferritin is measured. Ferritin can be fixed to a surface or suspended in solution. A concentration of reductant is chosen that, in the presence of a protein unfolding agent, leads to the release of iron in a conveniently measurable time, e.g., approximately 0.1-80 minutes. Suitable reductants include NADH (nicotimamide adenine dinucleotide) and FMN (flavin mononucleotide), both present in concentrations of approximately 2.5 mM. Other reductants can be used, including, without limitation, sulfhydryl reagents such as dithiothreitol and β-mercaptoethanol, and antioxidants such as lipoic acid or ascorbate.

Protein unfolding agents for testing (e.g., agents of interest) according to this aspect of the invention can be taken "off the shelf," e.g., the agents can include previously known and studied chemicals. Alternatively, a library of novel agents can be assembled or synthesized. The agents in the library can then be screened or selected for the ability to enhance iron release from ferritin, as described herein. In a variation of this aspect of the invention, one or more of the agents to be tested is rationally designed based on the 3-dimensional crystal and/or solution structures of ferritin as solved, e.g., by Takagi, H., et al., *J. Biol. Chem.* 273: 18685-18688 (1998) (PDB ID: 1BG7). Examples of agents designed based on the three dimensional structure of ferritin are peptides designed to bind to the pore, e.g., those peptides disclosed herein in (SEQ ID NOS:1-7). For recent reviews relating to the rational design of drugs, see Klebe, G., *J. Mol. Med.*, 78(5): 269-81 (2000); Bursavich, M. D. and Rich, D. H., *J. Med. Chem.* 45(3): 541-58 (2002). In another variation of this aspect of the invention, agents can be selected for their ability to preferentially bind to ferritin molecules which comprise "open" ferritin pores, as opposed to ferritin which is "closed" (Jin, W. et al, *Biochem.* 40: 7525-7532 (2001)). Such agents would be expected to stabilize ferritin in an "open" pore state, and thereby enhance iron release.

Methods of measuring the rate of iron release from ferritin are well known in the art. See, e.g., Jin, W. et al. (2001). Preferably the reaction of ferritin with potential protein unfolding agents is analyzed at physiologically relevant pH and salt conditions. A pH of about 6.0 to 8.0 is preferred, as is a sodium concentration of approximately 0.2 M. Sodium chloride (NaCl) is a preferred salt, but other physiologically relevant salts can be substituted or included in the reaction buffer. The buffer MOPS is preferred, but one skilled in the art will recognize that other buffers can be substituted.

In a preferred embodiment of the invention, iron release is detected using a colorimetric reagent. 2,2'-bipyridine and its derivatives are useful colorimetric chelators of iron. The concentrations of the reconstituted ferritin protein and of the calorimetric reagent are chosen such that: (a) the colorimetric agent is present in stoichiometrically higher concentration than the iron content contained in the ferritin protein; and (2) the color change that develops by the release of the iron leads to a conveniently measurable degree of color change.

Iron release can also be measured using fluorescent iron chelators, wherein the fluorescence of the chelator is quenched upon binding to iron. For example, chelation of iron by calcein results in measurable fluorescence quenching. See, e.g., Breuer, W., et al., *FEBS Lett* 382:304 (1996). Other chelators that exhibit fluorescence quenching upon binding to iron can also be used. See, e.g., Kuhn, M. et al., *Proc. SPIE-Int.l Soc. Opt. Eng.*, 2388: 238 (1995).

The initial rates of iron release and/or the total amount of iron release are measured in the absence of protein unfolding agent. Using this method of the invention, experimental data can be rapidly collected for potential protein unfolding agents. An effective concentration of a protein unfolding agent is one that results in at least a two-fold increase in the initial rate of iron release from ferritin, without causing generalized unfolding or denaturation of ferritin. The concentrations of protein unfolding agents, chelators, and reductants that are most effective for enhancing iron release can be determined by titration. A concentration of reductant should be used which leads to the release of iron in a conveniently measured time, e.g., within 80 minutes.

One skilled in the art will recognize that the invention can be used to screen many different types of agents for their ability to enhance iron release from ferritin. For example, a library of potentially useful agents of interest, e.g., protein unfolding agents, e.g., peptides, can be screened according to this method. The library can be synthesized in vitro, e.g., on a solid support. A suitable solid phase support can be selected on the basis of desired end use and suitability for various protocols. For example, for peptide synthesis, solid phase support can refer to resins such as polystyrene (e.g., PAM-resin obtained from Bachem Inc., Pennsylvania; Peninsula Laboratories, California; etc.), POLYHIPE® resin (obtained from Aminotech, Canada), polyamide resin (obtained from Peninsula Laboratories, California), polystyrene resin grafted with polyethylene glycol (TentaGel®, Rapp Polymere, Tubingen, Germany) or polydimethylacrylamide resin (obtained from Milligen/Biosearch, California). Solid supports also include microchips and grids, on which cDNAs, oligonucleotides, peptides, antibodies or other molecules are fixed in arrays. The surface of the grids can be composed of a wide variety of material including glass, plastic, silicon, gold, gelatin or nylon. Lockhart (2000) *Nature*, 405:827-836; Srinivas (2001) *Clin. Chem.*, 47:1901-1911, and further described herein.

As an alternative to chemical synthesis, phage display technology can be utilized to generate peptides that enhance the release of iron from ferritin (McCafferty, J. et al., *Nature* 348: 552-554 (1990); Marks, J., et al., *Biotechnology* 10: 779-783 (1992)). Peptides can be selected and/or screened for their binding affinity to ferritin pores in the unfolded or "open" state. The affinity of these peptides, and their effectiveness at enhancing iron release, can be improved by chain shuffling (Clackson, T. et al., *Nature* 352: 624-628 (1991)).

Alternatively, a commercially available phage display peptide library (e.g., Ph.D. library from New England Biolabs) can be screened for peptides that act as ferritin protein unfolding agents. In one embodiment, both wild type H ferritin and H-L134P mutant ferritin (an "open" pore ferritin) are fixed to a polylysine-coated microtiter plate. Since ferritin has 8 pores, at least one pore in a majority of the wells is exposed on the surface. At least three cycles of "panning" (binding, washing, elution of specifically bound ligand at low pH and amplification in phage host *E. coli* ER2537) is used to purify specific peptides that bind to wild-type ferritin. The ferritin binding peptides can be rescreened for binding to open-pore, mutant ferritin to identify peptides that bind to features of ferritin common to both open and closed pores. The peptides that are ferritin specific and specific for pores are tested to determine each peptides' effectiveness at increasing rates of iron release using wild type mineralized ferritin in the Fe release/chelation assay and, e.g., both bipyridyl and DFO as chelators.

An alternative embodiment uses a ferritin pore fragment (e.g., C/D helix) labeled with 35S-methionine as a target for peptide binding followed by chromatography (e.g., C18 reverse phage chromatography or high resolution gel filtration) isolation of radioactive complexes to identify pore binding peptides from a library. Peptides identified in this way are also analyzed with wild type ferritin in the Fe release to chelator analysis described above.

In another embodiment, ferritin itself can be fixed in arrays, allowing hundreds or thousands of iron release assays to be carried out in parallel. Different agents to be tested can be added to each ferritin-containing well in the array. A colorimetric chelator such as 2,2' bipyridine can be used to monitor iron release in a screen for useful agents, as described herein.

EXAMPLES

Example 1

Analysis of Enhanced Iron Release Effected by Low Concentrations of Triton-X-100, Urea, or Guanidine The global structure of ferritin has been shown to be stable to 6 M urea at neutral pH (Lavoie, D. J., Marcus, D. M., Otsuka, S., Listowsky, I. (1979) Biochim. Biophys. Acta 579, 359-366)(Otsuka, S., Listowsky, I., Niitsu, Y., Urushizaki, I. (1980) J. Biol. Chem. 255, 6234-6237) and temperatures to 85° C. (Stefanini, S., Cavallo, S., Wang, C. Q., Tataseo, P., Vecchini, P., Giartosio, A. & Chiancone, E. (1996) Arch Biochem Biophys 325, 58-64). Here we demonstrate the use of lower concentrations of protein unfolding agents, for example, 1.0 mM to 1 M urea or guanidine to "open" the ferritin pores as assessed by enhanced rates of Fe chelation. In addition, the conditions caused a 10° C. downshift of a helix/coil transition to 43° C. These methods for opening the ferritin pores can be used in the assays described herein for identification of agents useful for altering rates of iron release from ferritin. In addition, these results demonstrate the effectiveness of protein unfolding agents in increasing the rate of iron release from ferritin.

Briefly, as described in further detail below, recombinant ferritin was expressed, isolated, and mineralized. The mineralized, recombinant ferritin was incubated with a protein unfolding reagent (e.g., urea, guanidine, or Triton X-100). Chelator and reductant was then added to the reaction, and rates of iron release were monitored by UV absorbance detection of formation of Fe(II)-bipyridyl (A522 nm/sec).

Production of recombinant ferritin. Recombinant ferritin was expressed using bullfrog sequences as the kinetic properties have been particularly favorable for study (Takagi H., et al. (1998) J. Biol. Chem. 273:18685)(18)(19)(20). Crystallographic studies of frog and human ferritins (Trikha, J., Theil, E. C. & Allewell, N. M. (1995) J Mol Biol 248, 949-67) (Hempstead, P. D., Yewdall, S. J., Fernie, A. R., Lawson, D. M., Artymiuk, P. J., Rice, D. W., Ford, G. C., & Harrison, P. M. (1997) J. Mol. Biol. 268, 424-448) show very similar structures and mechanisms (Bou-Abdallah, F., Papaefthymiou, G. C., Scheswohl, D. M., Stanga, S. D., Arosio, P. & Chasteen, N. D. (2002) Biochem J. 364, 57-63)(Hwang, J., Krebs, C., Huynh, B. H., Edmondson, D. E., Theil, E. C. & Penner-Hahn, J. E. (2000) Science 287, 122-125)(18). The H-type ferritin was used because of the ease of analyzing functional integrity of protein preparations by UV-vis spectroscopy using the product of the ferroxidase reaction, in which L subunit ferritin is inactive. Two proteins were compared in the study: H-wild type and H-L134P, an "open" pore protein for which the crystal structure is known (Takagi H., et al. (1998) J. Biol. Chem. 273:18685). Sequences coding H-wild type and H-L134P ferritin were inserted into the vector pET-9a and expressed in *E. coli* BL21-DE3-PLysS (Stratagene®). The recombinant proteins were isolated as the 24-subunit assembly without Fe (<0.5/subunit) using methods previously described (20). All the protein preparations used showed maximal formation of the blue ferroxidase intermediate, a diferric peroxo complex, Fe(III)-O—O—Fe(III) (A 650 nm (18)(19)(Hwang, J., Krebs, C., Huynh, B. H., Edmondson, D. E., Theil, E. C. & Penner-Hahn, J. E. (2000) Science 287, 122-125) within 25 ms and decay to Fe(III)-O—Fe(III) products within 1 sec.

Mineralization of ferritin. Recombinant ferritin was mineralized by adding a freshly prepared, acidic solution of $FeSO_4$ (to minimize oxidation and hydrolysis) to apoferritin in buffer and incubating at room temperature for 1 hour and then overnight at 4° C., to complete hydrolysis of ferric mineral precursors (18). The final solution was 2.08 µM protein with 480 Fe/protein (24 Fe/subunit) in 0.1 M MOPS, 0.1M NaCl, pH=7. Sterile solutions of mineralized ferritin are stable for months to years.

Measurement of iron release rates. Rates of Fe exit from ferritin (rates of dissolving the Fe biomineral) were monitored as formation of Fe(II)-bipyridyl (A522 nm/sec). The reaction was started by mixing an equal volume of mineralized ferritin with an equal volume of a solution of a NADH (5 mM), FMN (5 mM), and bipyridyl (5 mM) as first described by Jones and Walsh (21). The initial rates of iron chelation were calculated by taking the linear ascending part of the multiphasic reaction curve, averaged from 3 independent assays/protein preparations and 2-3 independent protein preparations.

Triton X-100 and Urea. One set of reactions was treated with Triton X-100 at final concentrations of 0.1%, 1.0% or 10% (volume/volume). A second set of reactions was treated with urea at final concentrations of 1 mM, 10 mM, or 1M. A third set of reactions was treated with a control solution containing only buffer. All three sets of ferritin solutions were incubated further for 17-20 hours (i.e., overnight) at 4° C., then returned to room temperature. Iron release was initiated by the addition of 2.5 mM bipyridine, 2.5 mM NADH, and 2.5 mM FMN (final concentrations). The amount of iron released from ferritin was monitored at room temperature, over a period of one hour, by appearance of absorbance at 522 nm due to formation of the Fe(II)-bipyridyl complex.

Figure 1B:
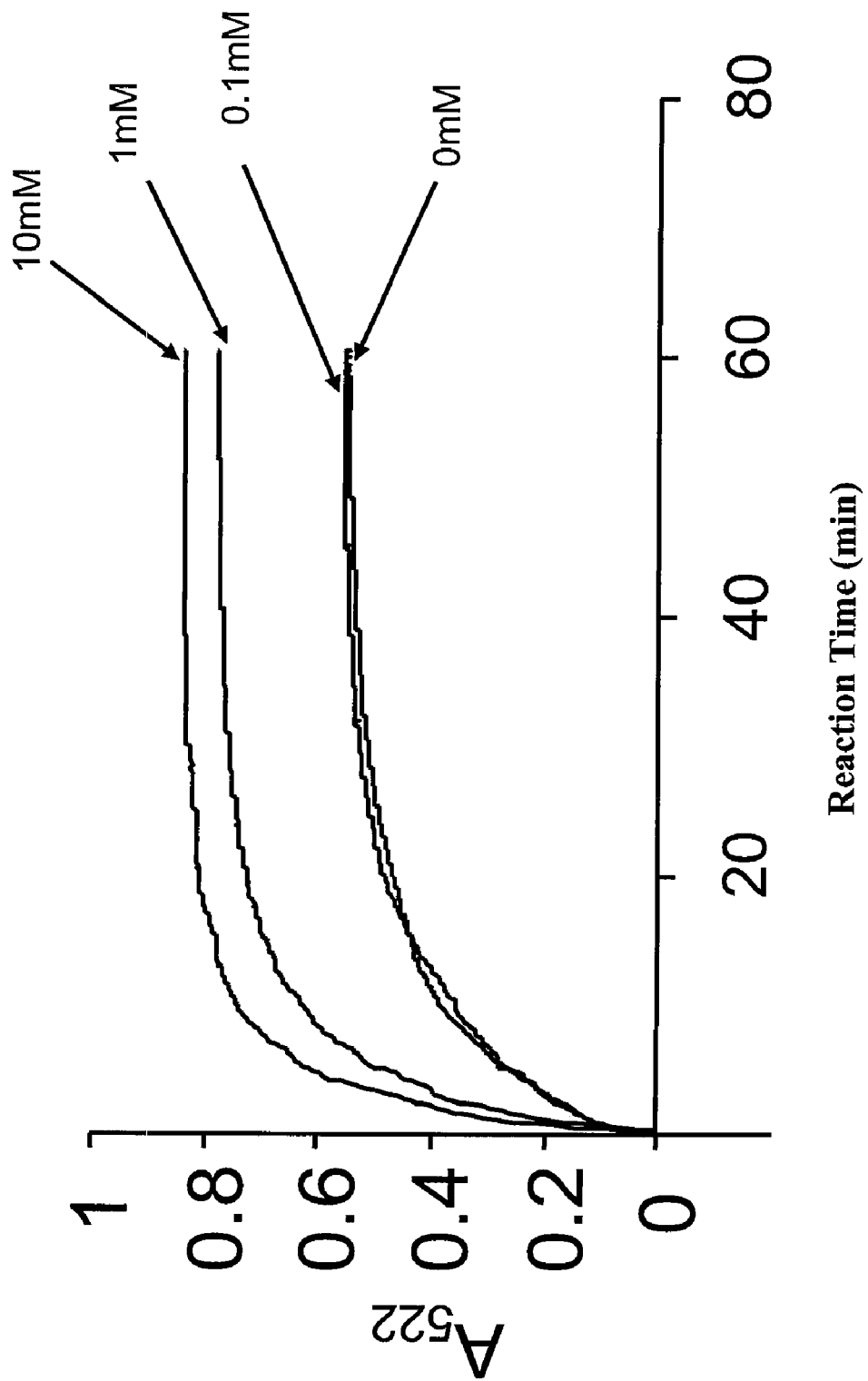
FIG. 1B is a progress curve for formation of Fe(II)-bipyridyl by ferritin after treatment with urea (0 mM, 1 mM, 10 mM and 1 M).

The enhancement of iron release by low concentrations of Triton X-100 and urea are shown in FIGS. 1A and 1B, respectively. The initial rates of iron release (from 0 to 2.0 minutes) were at least 2 fold greater in the presence of 1.0% or 10% Triton X-100, or 1 mM or 10 mM urea, relative to rates observed in the absence of these agents. The time required for release of 50% of the iron from ferritin by urea or Triton X-100 decreased by a factor of 10-20 fold (absorbance at 522 nm=0.4).

Urea, Guanidine HCl, and Triton X-100. The effects on iron release from ferritin of urea, guanidine hydrochloride, and Triton X-100 were studied by mixing solutions of the mineralized protein with a protein unfolding reagent and incubating at room temperature for 1 hour, followed by incubating overnight at 4° C. before adding reductant and chelator. The final concentrations were: 1.04 µM protein, 2.5 mM FNM, NADH and bipyridyl, 0.50 mM Fe, 0.05 M MOPS pH7, and 0.05 M NaCl. Final concentrations of urea were 1 mM, 10 mM, 1M, and 2M. Final concentrations of Triton X-100 were 1% and 10%. Final concentrations of guanidine-HCl were 0.1 mM, 1 mM, and 10 mM. The results are shown in FIG. 2.

Figure 2A:
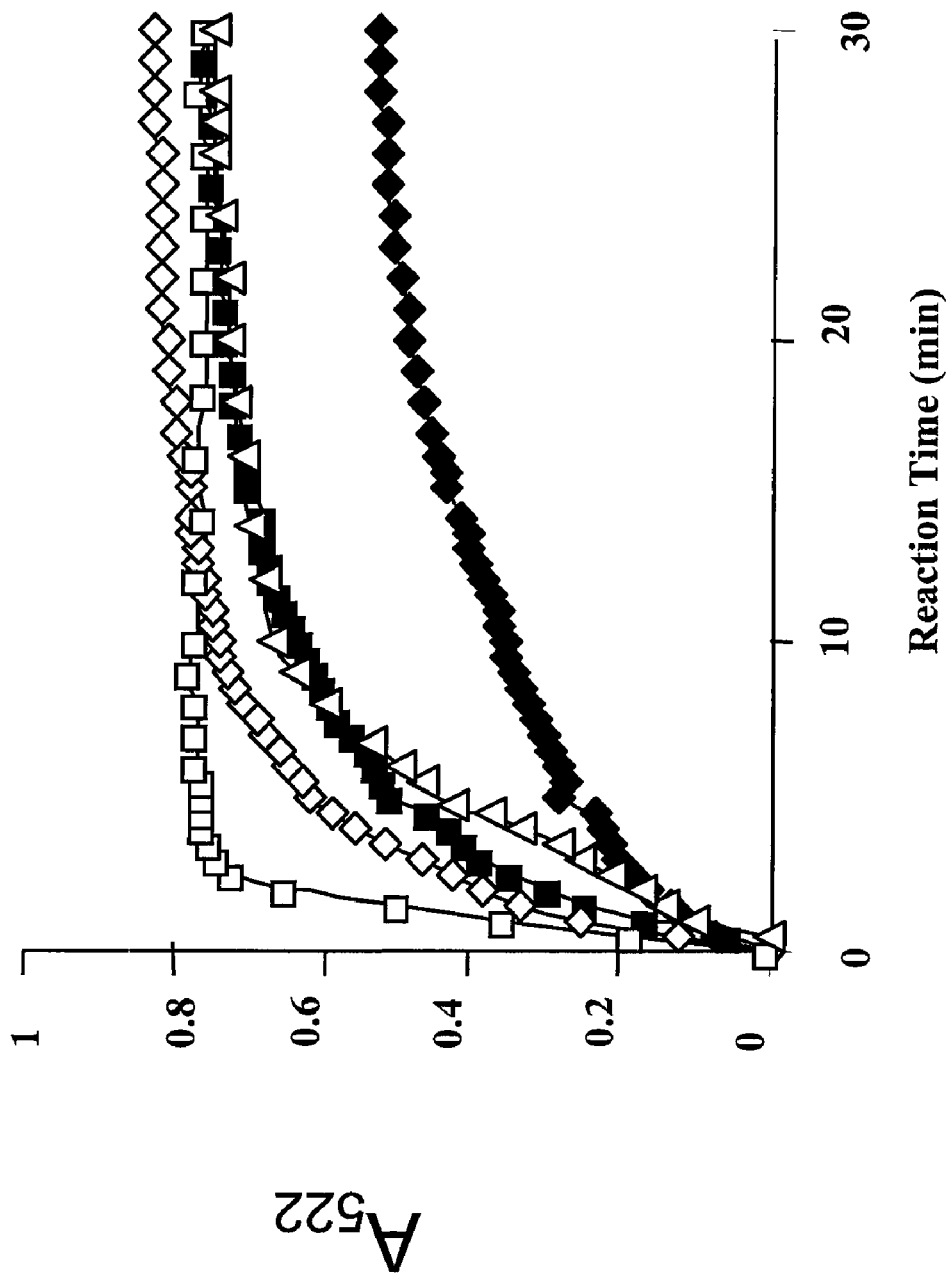
FIG. 2A is a progress curve for formation of Fe(II)-bipyridyl using the following concentrations of urea: ♦, 0; ■, 1 mM; ◇, 10 mM.; ☐,, 1 M; Δ, 2 M.
Figure 2B:
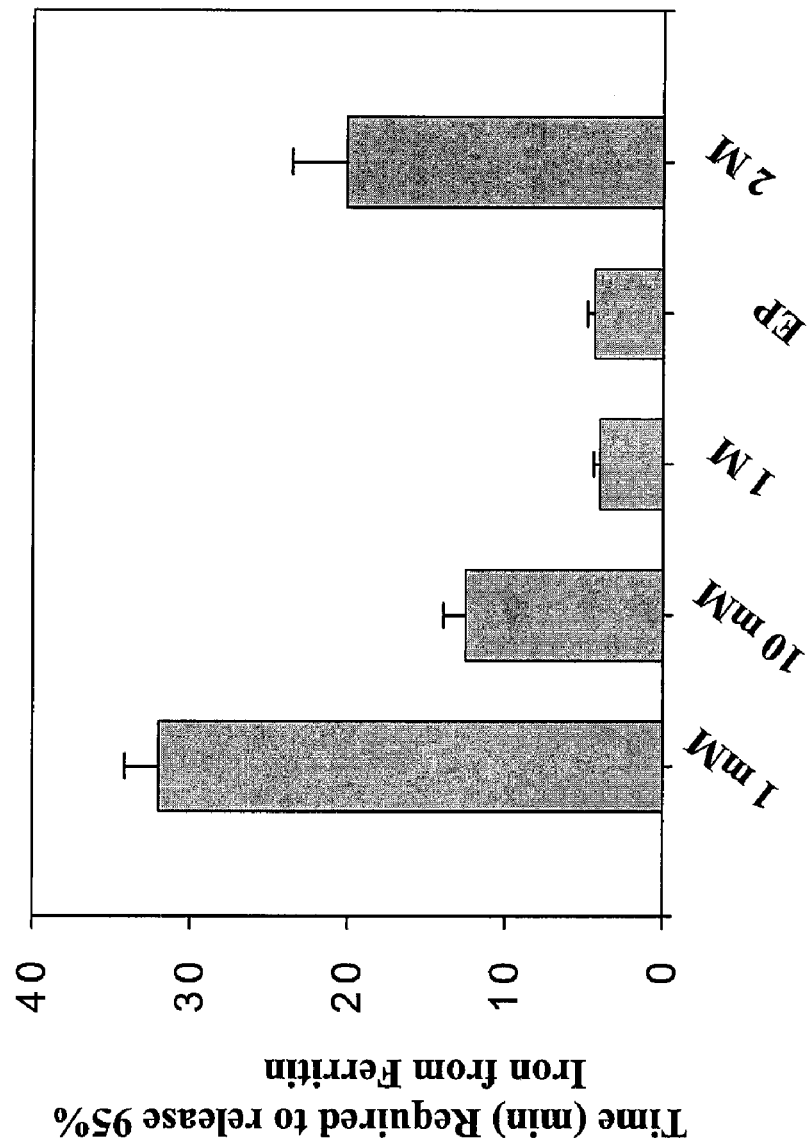
FIG. 2B is a bar graph illustrating the decrease in the time required to empty all the Fe from the ferritin mineral cavity in the presence of urea; in the absence of urea 150 minutes are required (Takagi H., et al. (1998) *J. Biol. Chem.* 273:18685); EP=Engineered Protein H-L134P.

As shown in FIG. 2A, millimolar concentrations of urea increased rates of Fe(II) chelation significantly, illustrating that ferritin pores are differentially sensitive to chaotropes. This is in contrast to the global structure of ferritin. At 1 mM urea, for example, the initial rate was $1.90\pm0.11\times10^{-3}$ Fe(II) bipyridyl mmole formed/second compared to $0.97\pm0.09\times10^{-3}$ mmole/second without urea. Fe(II)-bipyridyl formation increased with increasing concentration of urea up to 1M, where the initial rate was $4.68\pm0.06\times10^{-3}$ mmoles/second, a 4.81 fold increase over the initial rate without urea. At 2M urea, the initial rate decreased $1.02\pm0.11\times10^{-3}$ mmoles/second and a second phase appeared, which combined with the initial rate produced removal of >95% of the Fe in 20 minutes compared to 4 minutes for 1 M urea, 13 minutes for 10 mM urea, 33 minutes for 1 mM urea (FIG. 2B) and about 150 minutes in the absence of urea (Takagi H., et al. (1998) J. Biol. Chem. 273:18685). Fe(II) oxidation, a measure of Fe(II) entry and binding to the ferroxidase site, was slightly inhibited.

Also shown in FIG. 2A, the mineral dissolution rate was multi-phasic in the untreated protein as well as in 1 mM and 10 mM urea, albeit faster than without urea. High concentrations of urea produced a much simpler progress curve. At 1 M urea the progress curve is essentially linear, as it is for the H-L134P mutant protein. It has been shown that the helices are completely disordered at the C/D helix turn (amino acids 110-134) (Takagi H., et al. (1998) J. Biol. Chem. 273:18685).

At 2 M urea, the initial phase of Fe(II) bipyridyl was quickly replaced by a second, slower phase, indicating that further unfolding disrupted a channel or other structure between the pores and the protein cavity. The differences in the shapes of the progress curves observed for different concentrations of urea are paralleled by those for the SDM (site directed mutagenesis) proteins, where non conservative substitutions such as L 134G, L134P, or R72D+D122R behave kinetically like 1 M urea and conservative substitutions such as L134V, L134A, or L110V, or L 110A behave like 1 mM and 10 mM urea (Jin, W., Takagi, H., Pancorbo, N. M. & Theil, E. C. (2000) Biochemistry 40, 7525-7532) (FIG. 2). Such results indicate that the pore gate has two detentes, or as in the case of the FecA ferric citrate pore in E. coli (Helms), the pore has two gates. No Fe(II)-bipyridyl formed with urea-treated protein in the absence of FMN/NADH, which eliminates the possibility that urea changed the chelator reaction with the mineral.

Figure 2C:
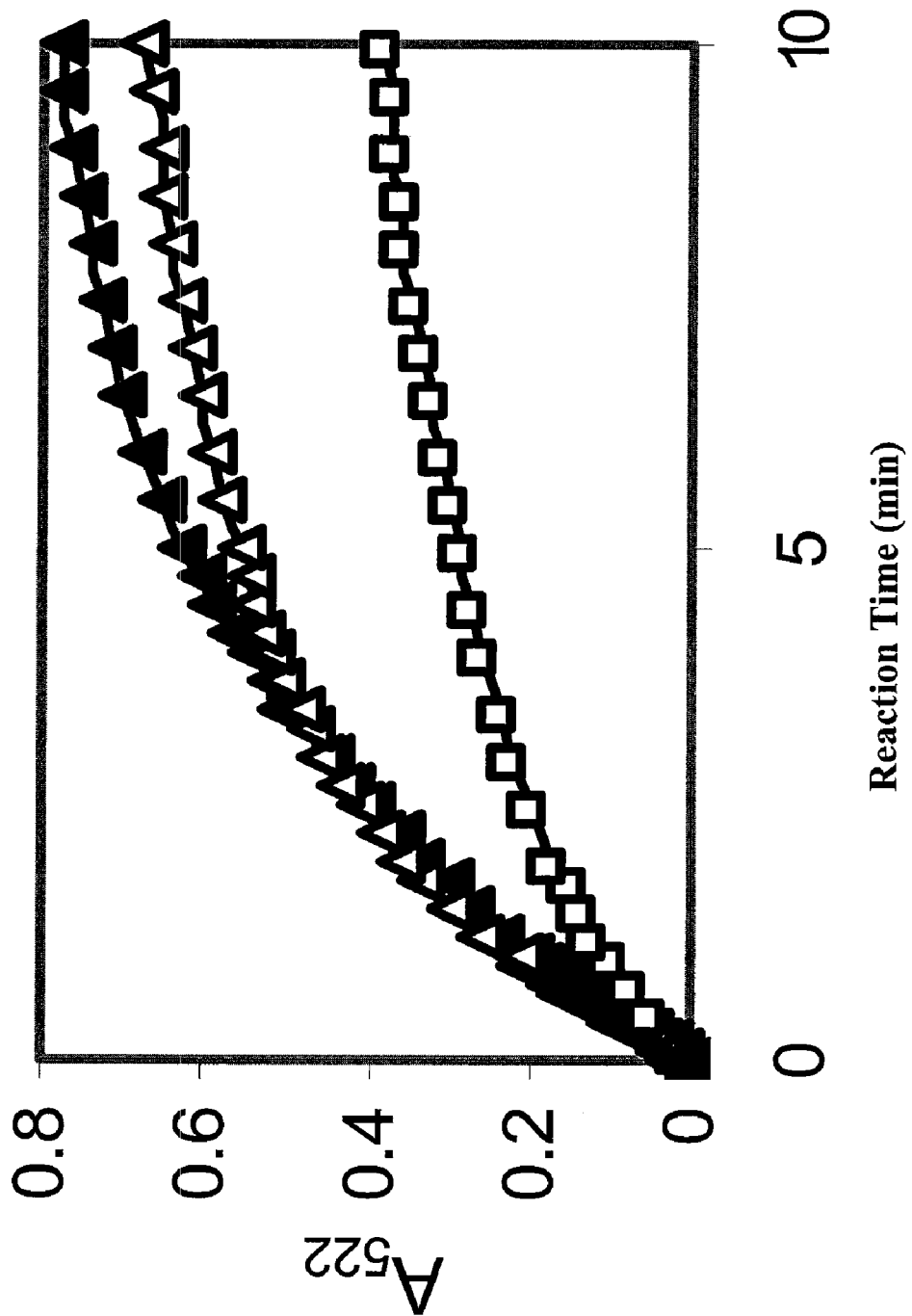
FIG. 2C is a progress curve for formation of Fe(II)-bipyridyl using the following concentrations Triton X-100: ☐,, zero; Δ, 1%; ▲, 10%.
Figure 2D:
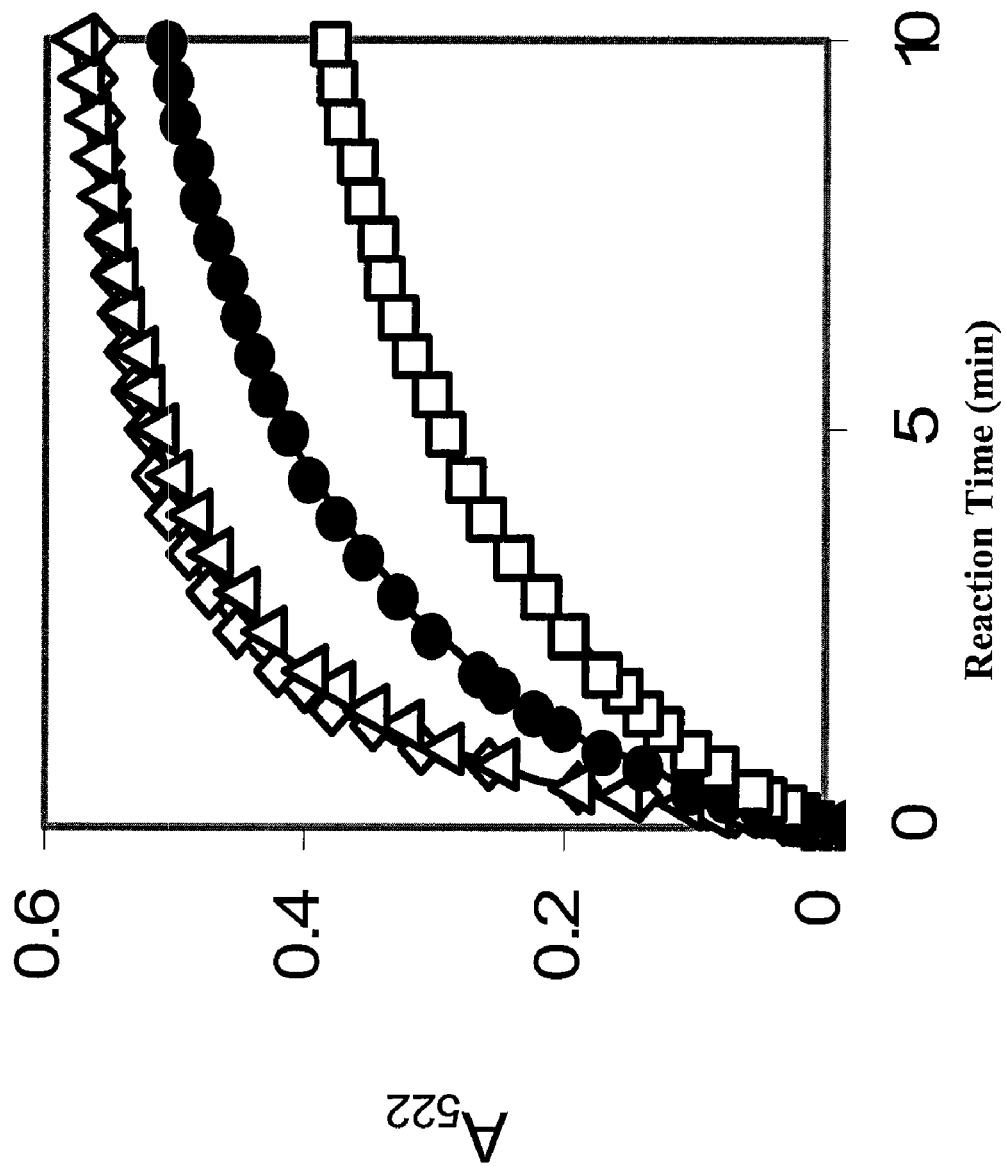
FIG. 2D is a progress curve for formation of Fe(II)-bipyridyl using the following concentrations of guanidine-HCl: ☐,, 0; ●, 0.1 mM; Δ, 1 mM; ◇, 10 mM.

Guanidine hydrochloride (Gd.HCl) and the nonionic detergent Triton X-100, two agents that disrupt protein hydrophobic interactions, were analyzed for effects on the formation rate of Fe(II)-bipyridyl, with NADH/FMN as the reductant. As shown in FIGS. 2C and 2D, the effect on ferritin iron release of Gd.HCl at 1 and 10 mM and Triton X-100 at 1% and 10% were comparable to the effect of 1 and 10 mM urea. Gd.HCl increased rates significantly even at 0.1 mM.

To determine if ionic strength might play a role in faster iron release, given that one of the interactions controlling the pore is the conserved ion pair Arg-72/Asp-122 (Jin, W., Takagi, H., Pancorbo, N. M. & Theil, E. C. (2000) Biochemistry 40, 7525-7532), the effect of 1M NaCl on the formation rate of Fe(II)-bipyridyl was analyzed using the same MOPS buffer for the standard conditions. Raising the ionic strength to 1M NaCl decreased both initial rate of iron Fe(II)-bipyridyl formation and total amount of Fe iron chelated (data not shown), indicating that high ionic strength inhibited access of reductant or chelator to Fe, "tightening" protein pores or changing chelator-Fe(II) binding or both.

Desferal® (desferrioxamine mesylate or DFO), a chelator of Fe(III), is currently the drug of choice to remove Fe from patients with excess tissue iron accumulated from monthly transfusions to treat betaglobin gene mutations (Sickle Cell Disease and Beta Thalassemia). Positive selection has made the mutations relatively common (<10%) in areas of the world where malaria is endemic. Iron in cells is thought to be Fe(II) during intracellular transfer and into and out of ferritin, because of the reducing environment in cells Desferal® removes little Fe from ferritin in solution (Crichton, R. R., Roman, F., Roland, F., Paques, E., Paques, A., Vandamme, E. (1980) J. Mol. Catalysis. 7, 267-276). In order to determine if unfolding ferritin pores increased Desferal® chelation of ferritin Fe, the chelator was substituted for bipyridyl in the mixture of NADH/FMN usually used. Formation of the Fe(III)—Desferal® complex was monitored at 430 nm, the absorbance maximum under the conditions used.

The effects of protein unfolding reagents on the rate of iron release of ferritin using Desferal® as a chelator are shown in Table 1. Fe(III)-Desferal® was readily detected in both H-Wild Type and H-L134P ferritin, where a rate increase of 8-fold occurred when the pores were locked in the open position (Takagi H., et al. (1998) J. Biol. Chem. 273:18685), emphasizing the contribution of chelator access to the rate of Fe removal. A lag was observed in the appearance of Fe(III)-Desferal®, which can be attributed to the time required for reoxidation of Fe(II) to Fe(III). Only 10% of the Fe could be chelated by Desferal®(D, in the absence of urea, which corresponds to earlier data obtained with tissue ferritin from horse spleen (26). However, even when the pore was "open" as in H-L134P, only 39% of the mineral Fe could be removed with Desferal®, compared to 98% with bipyridyl.

TABLE 1

|  | Initial Rate of Fe exit as Fe(III)- Desferal ® (mmole/s × $10^3$) | Initial Rate of Fe exit as Fe(II) -bipyridyl (mmole/s × $10^3$) |
| --- | --- | --- |
| H-Wild Type | 0.275 ± 0.041 | 0.972 ± 0.087 |
| H-L134P | 2.443 ± 0.032 | 3.934 ± 0.122 |

Example 2

Effect of Protein Unfolding Agents on Cell Viability as Determined by Trypan Blue Exclusion Test HeLa cells, cultured in DMEM medium with 10% FBS, were incubated with the protein unfolding agents for 24 hours at 37° C. in 12-well plates. Cells were treated with trypsin, fresh medium was added and the cells were suspended in the fresh DMEM medium with 10% FBS. Cell suspensions were mixed 1:4 with trypan blue in 0.85% NaCl (weight/volume), incubated 5 minutes at room temperature, then examined by light microscopy in a hemocytometer chamber. Blue cells are scored as non-viable. For each condition, 1-3 analyses were performed.

The results are shown in Table 2. No significant difference in cell viability was detected between cells incubated in normal medium and those treated with the indicated concentrations of urea or guanidine. Low concentrations of these two protein unfolding agents do not affect cell viability. The differences between treated and control cells do not appear to be significant given the variability of the analysis. The non-ionic detergent Triton-X-100 was toxic at concentrations of 1.0% and 10% (data not shown), indicating that lower concentrations or less toxic agents, e.g., non-ionic detergents, would have to be developed for treatment.

TABLE 2

| Conditions | % Nonviable cells | Average % nonviable cells |
| --- | --- | --- |
| HeLa cells | 7, 0, 3 | 3 |
| HeLa Cells + urea-1 mM | 11 | 11 |
| HeLa cells + guanidine-1 mM | 12, 0 | 6 |

Example 3

SDM Changes that Enhance Mineral Dissolution do not Affect Global Structure

Ferritin is very heat stable. In fact, heating is used to denature contaminating proteins during ferritin isolation from animal tissues (Theil, E. C. (2001) Ferritin (John Wiley & Sons, Chichester)). The major heat-induced disruption in ferritin structure occurs between 80° C. and 90° C., depending on the protein source (Stefanini, S., Cavallo, S., Wang, C. Q., Tataseo, P., Vecchini, P., Giartosio, A. & Chiancone, E. (1996) Arch Biochem Biophys 325, 58-64). To determine if the global temperature stability of ferritin is altered by changes that enhance mineral dissolution, the effect of SDM on global structure was measured as assayed by changes in UV absorbance.

Figure 3A:
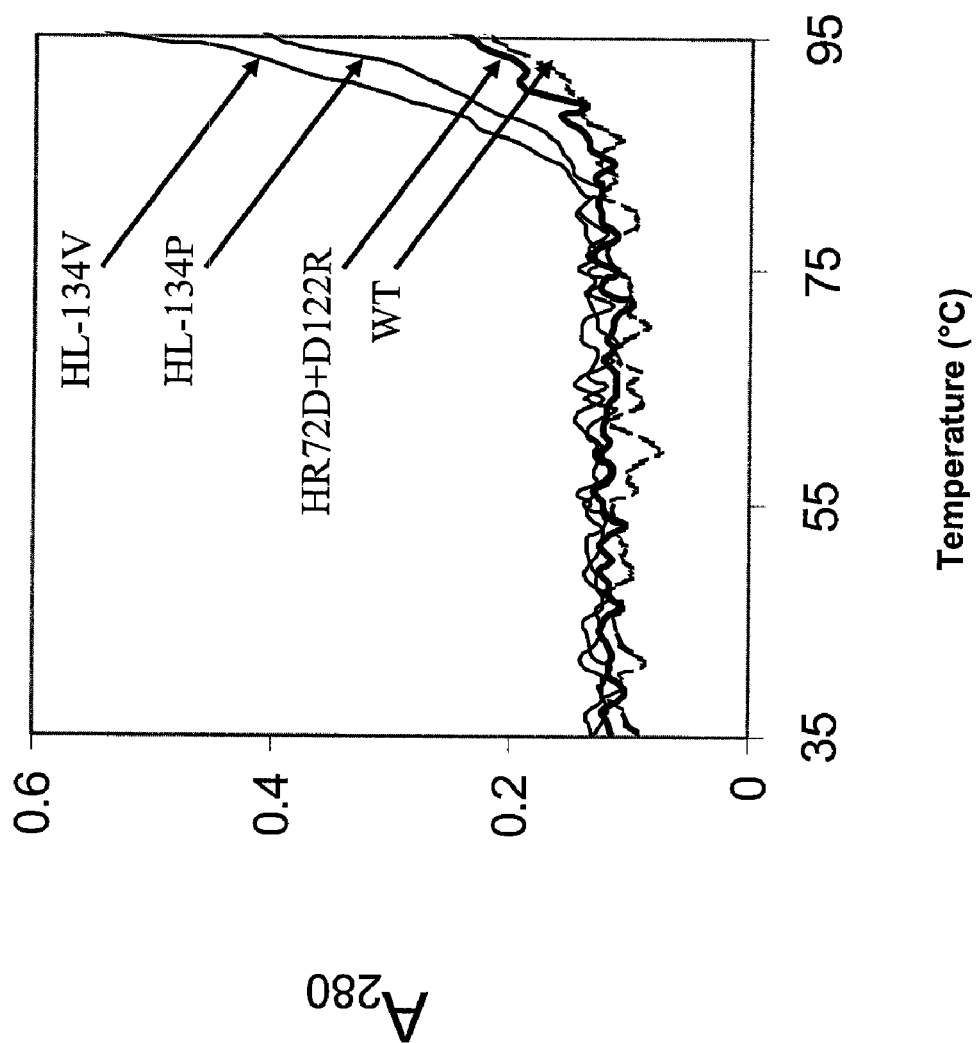
FIG. 3A is a UV-vis analysis of temperature transitions of global ferritin structure (A 280 nm) in wild type (WT) and pore mutants (L-134P, L134V, R72D+ D122R) between 35 and 95° C.

Global ferritin unfolding of wild-type ferritin and four mutants (H-R72D, D122R, H-L134P, and H-L134V) was monitored as changes in UV-vis absorbance at 280 nm, recorded on a Cary 100 Bio UV-vis spectrophotometer (Varian) over the temperature range 35° C. to 85° C. The results are shown in FIG. 3A.

No change in the UV-vis absorbance was observed between 35° C. and >85° C., for proteins representing the helix C/Helix D packing interaction (H-L134P, and H-L134V) and the ion pair between helix B and the C/D loop (H-R72D, D122R). The results emphasize that protein unfolding in ferritin can be localized around the pore with little influence on the rest of the protein.

Example 4

Low Concentrations of Protein Unfolding Agens Disrupt the Pore Subdomain of Ferritin The effects of protein unfolding agents on subdomain unfolding of ferritin were monitored as changes in the Circular Dichroism (CD) spectra. Both wild type ferritin (H-WT) and the open pore mutant H-L134P were analyzed. Solutions of mineralized protein ($2.08 \times 10^{-1}$ μM in 10 mM MOPS buffer, pH 7.0), were incubated with or without 1 mM urea overnight as described herein, and equilibrated for 10 minutes at the selected temperature before recording spectra between 300 nm to 200 nm. CD spectra recorded on a Pi-180 spectrophotometer (Applied Photophysics, Surrey, UK) over the temperature range of 5° C. to 65° C. Spectra were recorded in a cuvette with a 1 cm path length at protein concentrations of $2 \times 10^{-7}$ M, except for H-L134P, the protein with fully open pores in protein crystals, where the concentration was $4 \times 10^{-7}$ M to compensate for the lower signal at higher temperatures. Contributions of the solvent to the protein spectra were subtracted. Molar ellipticities at 220 nm were determined from the optical rotation, and the percent alpha helix content was calculated as described by Frére et al (Frere, V., Sourgen, F., Monnot, M., Troalen, F. & Fermandjian, S. (1995) J Biol Chem 270, 17502-17507) and Zhong and Johnson (Zhong, L. & Johnson, W. C. J. (1992) Proc Natl Acad Sci USA 89, 4462-4465). Curves were fit to the data using Sigmaplot 8.0. Fits and data matched with P<0.001. Data presented for H-L 134P ferritin are representative of two sets of measurements on one preparation and the data for the H-wild type protein, with and without urea, are representative of 3 independent protein preparations.

Figure 3B:
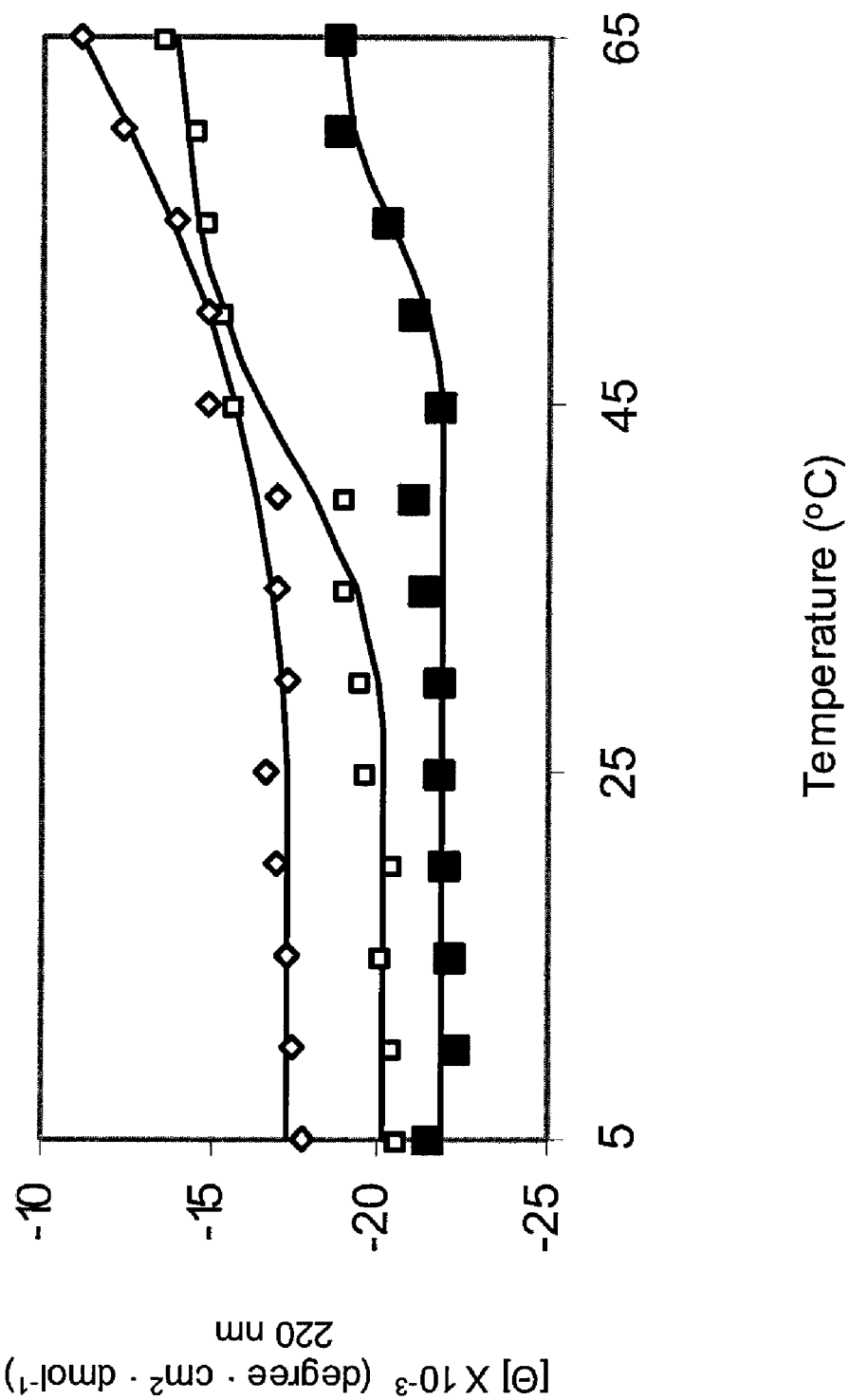
FIG. 3B is a CD analysis of subdomain temperature transitions below global melting in ferritin between 5 and 65° C.: ■, H-WT; ☐,, H-WT+1 mM urea; ◇, H-L134P.
Figure 3C:
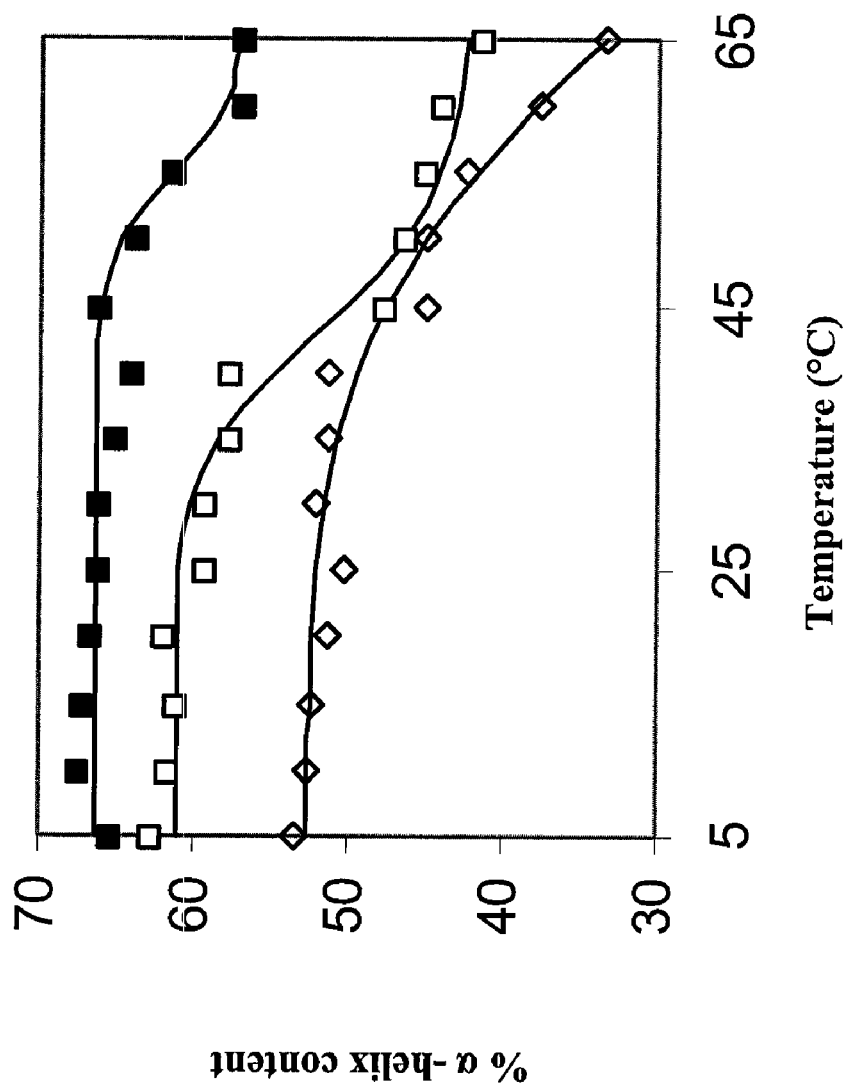
FIG. 3C is an analysis of alpha-helix content in ferritin between 5 and 65° C.: ■, H-WT: ☐,, H-WT+1 mM urea; ◇, H-L134P.
Figure 3D:
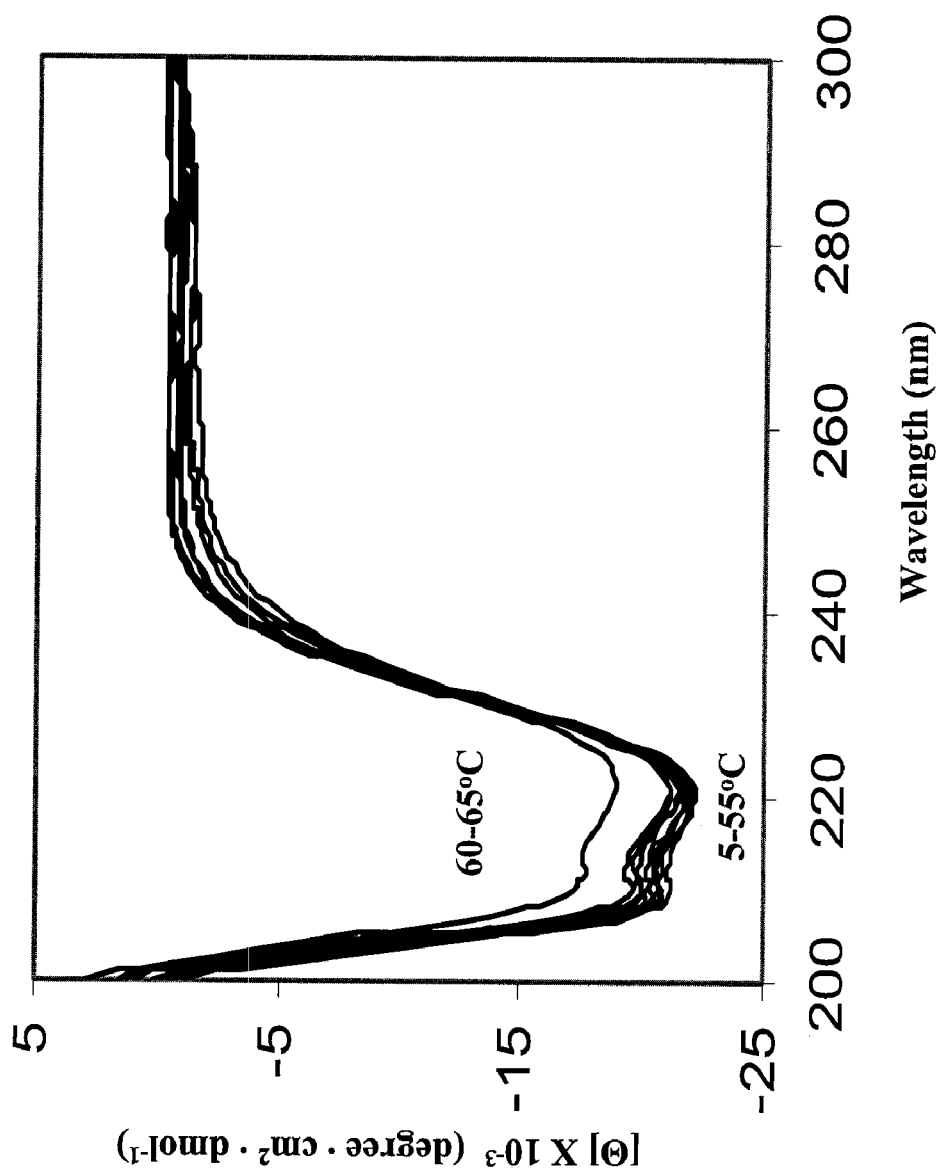
FIG. 3D is a CD spectra of H-WT ferritin at different temperatures.
Figure 3E:
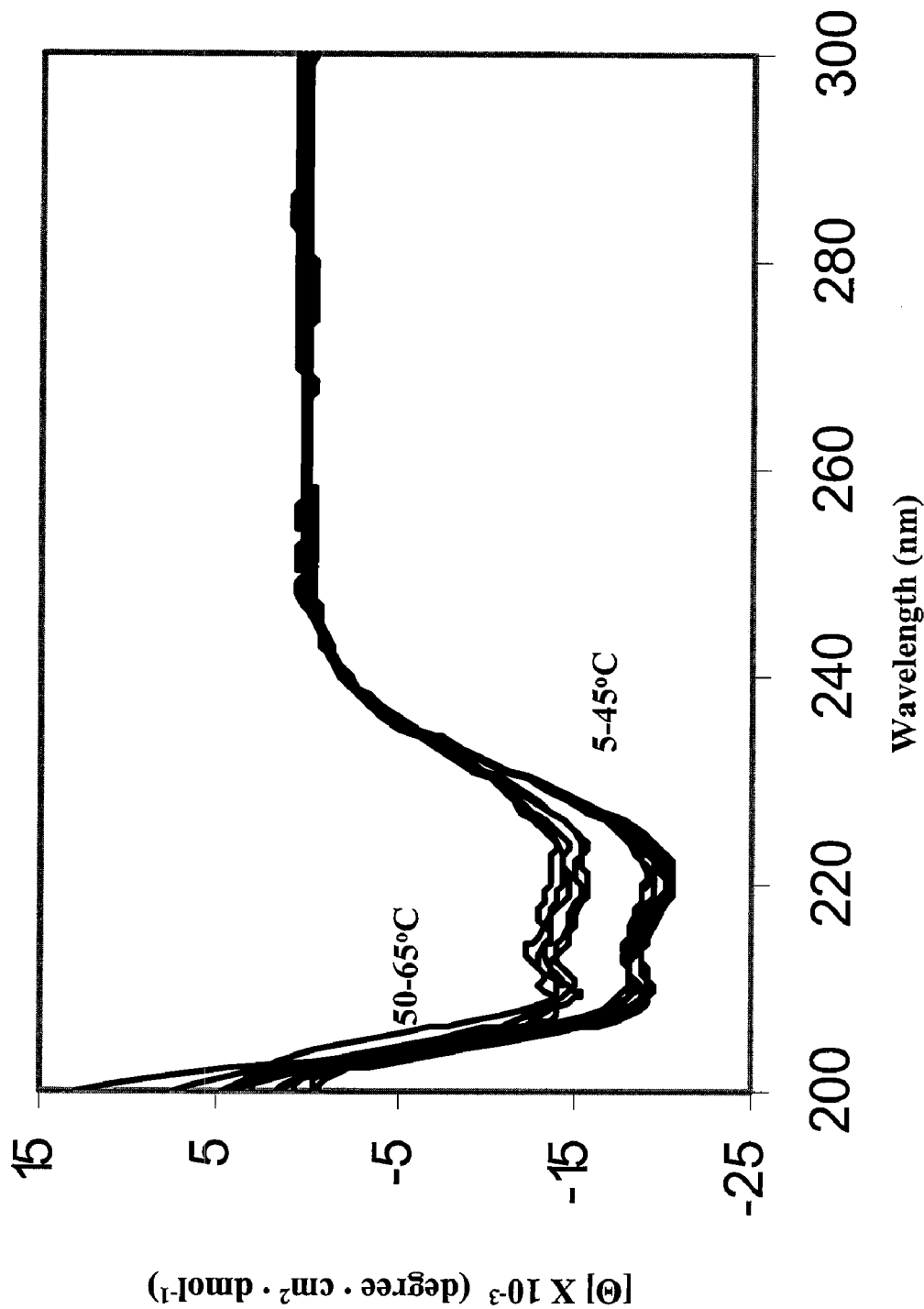
FIG. 3E is a CD spectra of H-WT ferritin+1 mM urea at different temperatures.
Figure 3F:
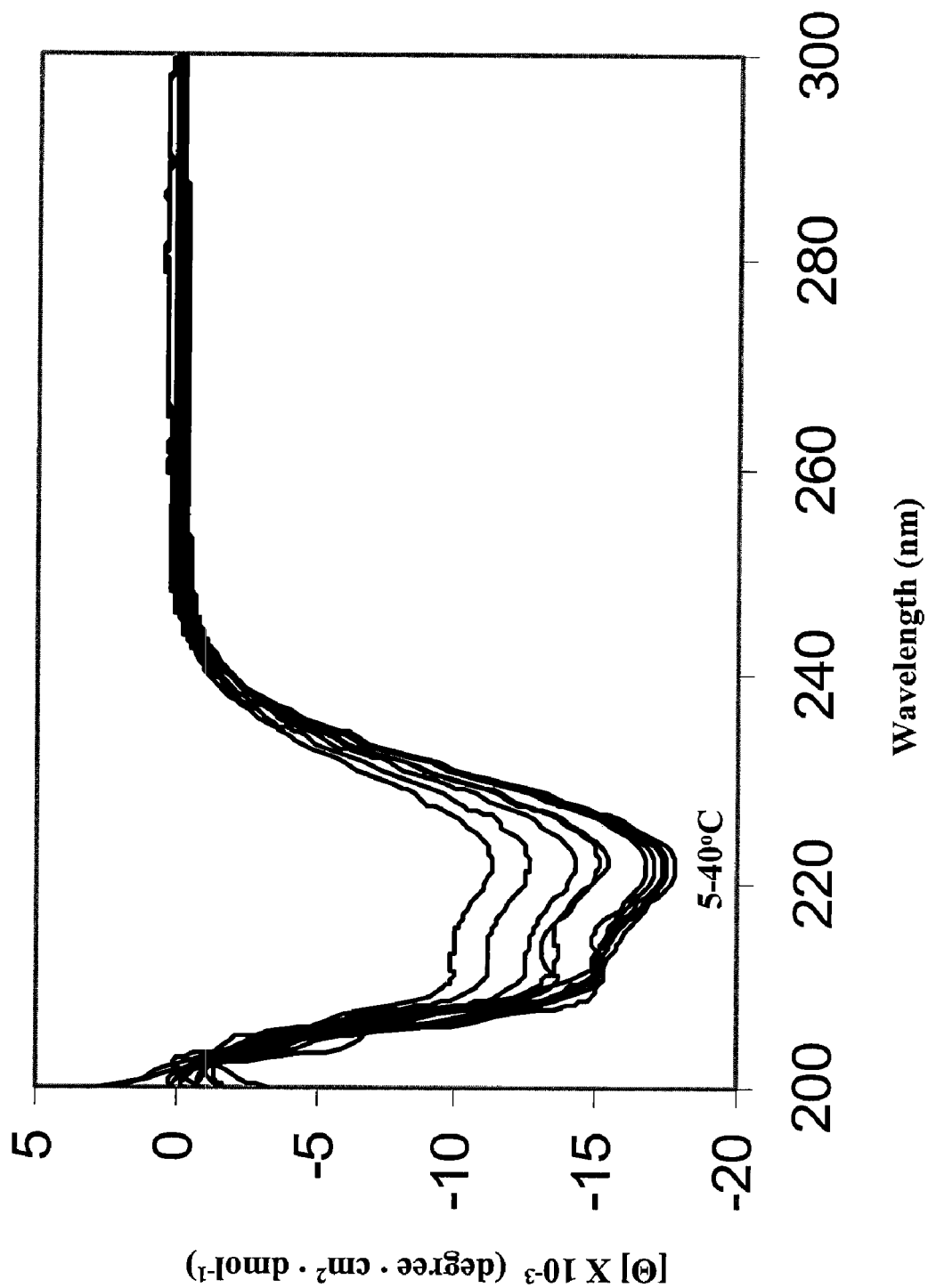
FIG. 3F is a CD spectra of H-L134P ferritin at different temperatures.

The results are presented in FIGS. 3B-F. The effect of temperature on subdomain temperature transitions below global melting is shown in FIG. 3B. The effect of temperature on percent alpha helix content is shown in FIG. 3C. The CD spectra at various temperatures are shown in FIG. 3D (H-WT), FIG. 3E (H-WT+1 mM urea) and FIG. 3F (H-L134P).

In the presence of 1 mM urea, a decrease in helix structure of WT ferritin was observed with a Tm (midpoint) of 41° C. that involved a helix loss of ~10% (FIG. 3C). A similar helix disruption was observed in the wild type protein in the absence of urea, except the temperature of the transition was increased 12° C. The coincidence of increased rate of formation of Fe(II)-bipyridyl with decreased temperature stability of a protein domain induced by 1 mM urea and the similarity between the % helix loss and the % helix accounted for by pore residues 110-119 and 126-134 (~10%), indicates that the temperature transition between 45° C. and 60° C. in H-Wild Type or 35° C.-50° C. in 1 mM urea involves the pore.

The temperature of the helix coil/transition in the pore was lower in both H-L134P protein and the wild type protein +1 mM urea (FIG. 3B) and is in the physiological range. For H-L134P the temperature for the beginning of the helix/coil transition was comparable to that for ferritin in 1 mM urea. However, the stability of the partially unfolded H-L 134P protein was lower, and loss of helix continued between 45° C. and 65° C. The change in formation of Fe(II)-bipyridyl was also larger for H-L134P ferritin than for wild type ferritin +1 mM urea, but was comparable to Wild Type H-ferritin with 1 M urea. Rates were $1.9\pm0.1\times10^{-3}$, $2.93\pm0.1\times10^{-3}$ and $4.68\pm0.06\times10^{-3}$ mmoles/second for H-WT ferritin+1 mM urea, H-L134P ferritin and Wild Type H ferritin+1M urea, respectively (FIGS. 2A, B). The local nature of the helix/coil transition induced by 1 mM urea observed between 35° C. and 50° C. (FIG. 3B), is emphasized by the small effects on other ferritin functions such as Fe uptake and mineralization where the rates were $0.67\pm0.01$ and $0.57\pm0.01$ $\Delta A_{650}s^{-1}$ for zero and 10 mM urea, respectively, for 480 Fe/protein.

Example 5

A Solid-Phase Assay for Screening Test Agents to Identify Agents that Alter Rates of Iron Release from Ferritin Ferritin is mineralized with ferrous ammonium sulfate as described (Takagi, H., Shi, D., Ha, Y., Allewell, N. M., and Theil, E. C. (1998) J. BIOL. CHEM. 273:18685-18688.) The mineralized ferritin is fixed to polysine-coated wells in microtiter plates, e.g., NUNC covalink NH96 well modules (Nalgene Nunc International #C478042) according to the manufacturers instructions. A subset of wells is left untreated with ferritin, as a negative control. The plates are then treated with a solution that includes an agent of interest; control wells are left untreated. This is followed by treatment with a chelating agent (e.g., bipyridyl) and a reductant (e.g., NADH and FMN) in the presence of air. Formation of the Fe-chelator (e.g., Fe(II)-bipyridyl or Fe(III)-desferrioxamine) complex is monitored by measurement of absorbance (e.g., A510) at appropriate time intervals (e.g., 1, 5 and 20 minutes) using a plate reader (e.g., Amersham Pharmacia). Test agents that include protein unfolding agents coupled with chelators are tested in the same way, except the bipyridyl is omitted from the solution and the formation of Fe-chelator complex is analyzed.

An agent that alters the rate of rate of iron release from ferritin is identified by selecting test agents that exhibit increased rates of Fe-chelator formation in comparison to negative controls (e.g., wells without protein unfolding agent).

Example 6

Coupling a Protein Unfolding Agent with a Chelator

Briefly, carbamic acid is coupled to desferrioxamine using t-boc. Standard methods are used for preparation of the t-Boc carbamic acid and removal of the t-Boc group after coupling (Aldrich Technical bulletin 19, 337-2; A. C. Spivey, A. Maddaford, "Protecting Groups" in *Annual Reports on the Progress of Chemistry*, Section B, Organic Chemistry vol 95, Ed. J. A. Joule, RSC, Cambridge, 1999, 95, 83-95).

For preparation of t-Boc carbamic acid, the amino group of benzyl carbamate is blocked with tert-butyloxycarbonyl using commercially available benzyl carbamate (e.g. Sigma Aldrich cat #21756) and the Boc-ON reagent (2-(tert-Butoxycarbonyloxyimino)-2-phenylacetonitrile, Sigma-Aldrich cat #15475). The benzyl group is selectively removed. In some embodiment the methods can include the use of tetrabutylammonium hydroxide (40% aqueous) in dimethylfuran or tetrahydrofuran at 0° C.

Alternatively, a t-boc derivative of ammonium carbamate (Fluka/Sigma-Aldrich product #09699) is prepared using the Boc-ON reagent (2-(tert-butoxycarbonyloxyimino)-2-phenylacetonitrile, Sigma Aldrich product # 15475). The product has no benzyl groups to remove.

The product is coupled with the chelator (e.g., desferrioxamine, Sigma Aldrich Product Number: D9533 Deferoxamine mesylate salt). Coupling is accomplished using carbodiimide coupling techniques, e.g., using resin-bound carbodiimide reagent (Argonaut technical bulletin 501; Rebek J, Feitler D. "Peptide synthesis with carbodiimide" Int J. Pept. Protein Res (1975) 7(2): 167). After coupling, the t-boc group is selectively removed under mildly acidic conditions.

The product, a protein unfolding agent (e.g., urea) coupled to a chelator (e.g., desferrioxamine) is used in the methods and compositions of the present invention.

All references, issued patents and patent applications cited within the body of the instant specification are hereby incorporated by reference in their entirety, for all purposes.

What is claimed is:

1. A composition comprising a protein unfolding agent, a reducing agent, and an iron chelator, wherein the protein unfolding agent is selected from the group consisting of a non-detergent chaotropic agent comprising urea or guanidine, the peptide consisting of SEQ ID NO: 1, the peptide consisting of SEQ ID NO: 2, the peptide consisting of SEQ ID NO: 3, the peptide consisting of SEQ ID NO: 4, the peptide consisting of SEQ ID NO: 5, the peptide consisting of SEQ ID NO: 6, and the peptide consisting of SEQ ID NO: 7; wherein the iron chelator is selected from the group consisting of 2,2' bipyridine or desferrioxamine; and wherein the reducing agent is selected from the group consisting of NADH, FMN, dithiothreitol, β-mercaptoethanol, lipoic acid, and ascorbate.

2. The composition of claim 1, wherein the protein unfolding agent is the peptide consisting of SEQ ID NO: 1.

3. The composition of claim 1, wherein the iron chelator is desferrioxamine.

4. The composition of claim 1, wherein the protein unfolding agent is a peptide and the peptide and the iron chelator are covalently coupled.

5. The composition of claim 1, wherein the protein unfolding agent is the peptide consisting of SEQ ID NO: 1 and the iron chelator is desferrioxamine and the protein unfolding agent and the iron chelator are covalently coupled.

6. An isolated polypeptide consisting of SEQ ID NO:1.

7. The composition of claim 1, wherein the composition enhances iron release from a ferritin comprising a ferritin pore and a site of iron release in vitro, and wherein the protein unfolding agent locally alters the ferritin structure at the ferritin pore or destabilizes the site of iron release, but does not promote ferritin disassembly, generalized unfolding, or global denaturation.

8. The composition of claim 7, wherein the composition enhances by 2 fold an initial rate of iron release from the ferritin.

9. The composition of claim 7, wherein said composition decreases by 10-fold a time to achieve a 20-50% iron release from the ferritin.

10. The composition of claim 1, wherein the chaotropic agent comprises a concentration of 1-10 mM.

11. The composition of claim 1, wherein the iron chelator comprises 2,2' bipyridine.

12. The composition of claim 1, wherein the iron chelator comprises desferrioxamine.

13. The composition of claim 1, wherein the iron chelator comprises a colorimetric indicator of iron binding.

14. The composition of claim 1, wherein the protein unfolding agent comprises urea and the iron chelator comprises desferrioxamine.

* * * * *

UNITED STATES PATENT AND TRADEMARK OFFICE
CERTIFICATE OF CORRECTION

PATENT NO. : 7,893,024 B2  
APPLICATION NO. : 11/565456  
DATED : February 22, 2011  
INVENTOR(S) : Elizabeth Theil Page 1 of 1

It is certified that error appears in the above-identified patent and that said Letters Patent is hereby corrected as shown below:

In the Specification

Column 1, after the heading STATEMENT REGARDING FEDERALLY SPONSORED RESEARCH OR DEVELOPMENT, replace the paragraph on lines 16-18 with the following paragraph:

-- This invention was made with government support under grant no. DK0251 from the National Institutes of Health. The government has certain rights in this invention. --

Signed and Sealed this
Fourteenth Day of October, 2014

Michelle K. Lee
*Deputy Director of the United States Patent and Trademark Office*